(12) United States Patent
Wynbrandt et al.

(10) Patent No.: US 10,321,859 B1
(45) Date of Patent: Jun. 18, 2019

(54) SYSTEMS AND METHODS FOR CAPTURING AND ANALYZING HYPOGLYCEMIC EVENT DATA

(71) Applicant: Glooko Inc., Palo Alto, CA (US)

(72) Inventors: Samuel Wynbrandt, Palo Alto, CA (US); Rita Sharma, Palo Alto, CA (US); Daniel Todorov, Palo Alto, CA (US)

(73) Assignee: Glooko Inc., Palo Alto, CA (US)

( * ) Notice: Subject to any disclaimer, the term of this patent is extended or adjusted under 35 U.S.C. 154(b) by 909 days.

(21) Appl. No.: 14/631,733

(22) Filed: Feb. 25, 2015

Related U.S. Application Data

(60) Provisional application No. 61/944,517, filed on Feb. 25, 2014.

(51) Int. Cl.
  *G06F 19/10*  (2011.01)
  *A61B 5/145* (2006.01)
  *A61B 5/00*  (2006.01)

(52) U.S. Cl.
  CPC ........ *A61B 5/14532* (2013.01); *A61B 5/7275* (2013.01); *A61B 5/7282* (2013.01); *A61B 5/7435* (2013.01); *A61B 5/7475* (2013.01)

(58) Field of Classification Search
None
See application file for complete search history.

*Primary Examiner* — Larry D Riggs, II
(74) *Attorney, Agent, or Firm* — Morgan, Lewis & Bockius LLP

(57) ABSTRACT

Systems, methods, and computer readable storage media manage low blood glucose levels. The system receives blood glucose readings, where each reading includes a blood glucose value and a respective timestamp. The system compares each blood glucose reading to a predefined hypoglycemic event threshold, and identifies hypoglycemic events when a respective blood glucose reading is below the predefined hypoglycemic event threshold. For at least a subset of the identified hypoglycemic events, the system prompts a user for information associated with each hypoglycemic event. The information requested includes one or more of: symptoms associated with the respective hypoglycemic event; perceived causes of the respective hypoglycemic event; and treatment for the respective hypoglycemic event. In response to the prompting, the system obtains feedback about the identified hypoglycemic events and provides a report that includes at least a subset of the obtained feedback.

25 Claims, 22 Drawing Sheets

What caused you to feel hypo?

[select all that apply]

Excess Insulin | Excess Medication | Exercise | Delayed Meal

Incorrect Carb Calc | Schedule Change | Alcohol | Don't Know

Hypo Survey Summary

[tap save when you are finished]

Symptoms  540-1

Trembling    Nervous

Causes  540-2

Excess
Medication

Treatments  540-3

Glucose
Tablet

SYSTEMS AND METHODS FOR CAPTURING AND ANALYZING HYPOGLYCEMIC EVENT DATA

RELATED APPLICATION

This application claims priority to U.S. Provisional Application Ser. No. 61/944,517, filed Feb. 25, 2014, entitled "System and Method for Capturing Hypoglycemic Event Data," which is incorporated by reference herein in its entirety.

TECHNICAL FIELD

The disclosed implementations relate generally to managing hypoglycemic events, and more particularly to a system for obtaining, analyzing, and presenting hypoglycemic data.

BACKGROUND

Diabetes is taking a growing toll on the social and economic wellbeing. For example, in the United States, 8.3% of the population, an equivalent of 25.8 million children and adults, are diagnosed with the condition. In 2012, diagnosed diabetes incurred a cost of $245 billion, up 41% from 2007. Hypoglycemia-related hospitalizations cost as much as $48,000 dollars per event, which adds up to billions of dollars annually.

Traditionally, for people with diabetes, regular blood glucose level testing has been used to obtain blood glucose readings and to monitor lifestyle effects on blood glucose level. For example, some healthcare professionals may instruct a patient to obtain blood glucose readings six to twelve times a day so that the patient may observe the changes associated with particular events or time of the day. In order to obtain blood glucose readings, the patient can input blood samples into a glucose meter. The glucose meter then analyzes the blood samples and generates blood glucose readings.

Some glucose meters have limited tagging ability to associate one or more readings with attributes, such as date and time or whether the reading was immediately after a meal. However, such limited tagging ability cannot provide a clear picture of life style patterns related to a patient's blood glucose readings before, during, and after hypoglycemic events. Some conventional diabetes management systems provide limited hypoglycemic data analysis, and do not relate a patient's blood glucose readings with hypoglycemic events. Doctors and patients are often not recording symptoms, causes, and treatments properly, and thus fail to recognize lifestyle patterns that cause hypoglycemic events.

SUMMARY

The present disclosure is directed toward systems and methods that overcome the limitations and disadvantages described above by recording hypoglycemic data, analyzing the recorded data, and presenting the analysis result to raise hypo awareness. As used herein, the term "hypo" is used as shorthand for the terms "hypoglycemia" and "hypoglycemic." Using the systems in accordance with some implementations, providers, such as doctors and nurses, can determine patients' hypo unawareness and adjust patients' treatment plans accordingly. In addition, using the systems and methods in accordance with some implementations, patients can be more aware of their hypoglycemic events (i.e., when blood glucose levels are too low) and symptoms so that they can be trained to avoid hypoglycemia and/or take preventative action to stop these events from occurring in the future.

In accordance with some implementations, a method for managing low blood glucose levels is performed at a computer system having one or more processors, a display device, and memory storing one or more programs configured for execution by the one or more processors. The method includes first receiving a plurality of blood glucose readings for a person. In some implementations, each reading includes: a blood glucose value and a timestamp indicating when the respective reading was taken. The method also includes comparing each blood glucose reading of the plurality to a predefined hypoglycemic event threshold, and identifying a hypoglycemic event when a respective blood glucose reading is below the predefined hypoglycemic event threshold. For at least a subset of the identified hypoglycemic events, the method includes prompting the person to provide information associated with each hypoglycemic event. In some implementations, the information requested includes one or more of: symptoms associated with the respective hypoglycemic event, perceived causes of the respective hypoglycemic event, and treatment for the respective hypoglycemic event. In response to the prompting, the method also includes obtaining feedback from the person about the identified hypoglycemic events using a graphical user interface on the display device and providing a report on the display device that includes at least a subset of the obtained feedback.

In accordance with some implementations, the obtained feedback includes feedback regarding symptoms, feedback regarding causes, and feedback regarding treatment.

In accordance with some implementations, the person is prompted to provide information only for hypoglycemic events that are less than two weeks old.

In accordance with some implementations, the method for managing low blood glucose levels further includes determining that a severe hypoglycemic event occurred when the person indicates that assistance was required.

In accordance with some implementations, the predefined hypoglycemic threshold is defined as a fixed value, set by the person, or set by a doctor.

In accordance with some implementations, each blood glucose reading that is below the predefined hypoglycemic event threshold is identified as a distinct hypoglycemic event.

In accordance with some implementations, a plurality of blood glucose readings that are below the predefined hypoglycemic event threshold comprise a single hypoglycemic event when the timestamps of the blood glucose readings are within a two hour time period.

In accordance with some implementations, the provided report includes a hypo awareness grid. In the hypoglycemic awareness grid, in some implementations, one axis of the grid shows blood glucose level, a second axis of the grid shows reported symptoms, and each entry in the grid indicates how many hypoglycemic events had a specific (glucose level, symptom) pair.

In accordance with some implementations, the provided report includes a graphical presentation of information regarding blood glucose levels before and after one or more hypoglycemic events.

In accordance with some implementations, prompting the person to provide information associated with each hypoglycemic event includes displaying a plurality of hypoglycemic event symptom icons and recording user selection of one or more of the plurality of hypoglycemic event symptom icons.

In accordance with some implementations, prompting the person to provide information associated with each hypoglycemic event includes displaying a plurality of hypoglycemic event cause icons and recording user selection of one or more of the plurality of hypoglycemic event cause icons.

In accordance with some implementations, prompting the person to provide information associated with each hypoglycemic event includes displaying a plurality of hypoglycemic event treatment icons and recording user selection of one or more of the plurality of hypoglycemic event treatment icons.

In accordance with some implementations, the method for managing low blood glucose levels further includes analyzing the hypoglycemic events and the obtained feedback to identify one or more patterns of hypoglycemic events and including the identified patterns of hypoglycemic events in the provided report.

In accordance with some implementations, the method for managing low blood glucose levels further includes transmitting the received blood glucose readings and obtained feedback to a second computing device to identify one or more patterns of hypoglycemic events.

In accordance with some implementations, the identified patterns include a correlation between hypoglycemic events and time of day or day or week.

In accordance with some implementations, the identified patterns indicate that the person is unaware when low blood glucose levels are occurring.

In accordance with some implementations, the provided report includes one or more recommended changes to activities of the person.

In accordance with some implementations, a computer system for managing low blood glucose levels includes: one or more processors; a display device; and memory storing one or more programs configured for execution by the one or more processors including instructions for: receiving a plurality of blood glucose readings for a person. In some implementations, each reading includes a blood glucose value and a timestamp indicating when the respective reading was taken. The instructions also include comparing each blood glucose reading of the plurality to a predefined hypoglycemic event threshold, and identifying a hypoglycemic event when a respective blood glucose reading is below the predefined hypoglycemic event threshold. In addition, for at least a subset of the identified hypoglycemic events, the instructions include prompting the person to provide information associated with each hypoglycemic event. In some implementations, the information requested includes one or more of: symptoms associated with the respective hypoglycemic event, perceived causes of the respective hypoglycemic event, and treatment for the respective hypoglycemic event. In addition, the instructions include, in response to the prompting, obtaining feedback using a graphical user interface on the display device and providing a report on the display device that includes at least a subset of the obtained feedback.

In accordance with some implementations, a method for managing low blood glucose levels is performed at a computer system having one or more processors and memory storing one or more programs configured for execution by the one or more processors. The method includes first receiving a plurality of blood glucose readings for a person. In some implementations, each reading includes: a blood glucose value and a timestamp indicating when the respective reading was taken. For at least a subset of the blood glucose readings, the method includes receiving contemporaneous information about the person that specifies: hypoglycemic symptoms associated with the respective blood glucose reading, perceived causes of hypoglycemia at the time of the respective blood glucose reading, and treatment for hypoglycemia at the time of the respective blood glucose reading. The method also includes determining that one or more of the blood glucose readings represent hypoglycemic events when a respective blood glucose reading is below a predefined hypoglycemic event threshold, analyzing the hypoglycemic events and the contemporaneous information to identify one or more patterns of hypoglycemic events, and providing a report that includes the identified patterns of hypoglycemic events and at least a subset of the contemporaneous information.

In accordance with some implementations, the method further includes determining that a severe hypoglycemic event occurred when the contemporaneous information indicates that assistance was required.

In accordance with some implementations, the provided report includes a hypo awareness grid. In some implementations, one axis of the grid shows blood glucose level, a second axis of the grid shows reported symptoms, and each entry in the grid indicates how many hypoglycemic events had a specific (glucose level, symptom) pair.

In accordance with some implementations, the provided report includes a graphical presentation of information regarding blood glucose levels before and after one or more hypoglycemic events.

In accordance with some implementations, the identified patterns include a correlation between hypoglycemic events and time of day or day or week.

In accordance with some implementations, the identified patterns indicate that the person is unaware when low blood glucose levels are occurring.

In accordance with some implementations, the provided report includes one or more recommended changes to activities of the person.

One aspect of the disclosure is a method performed on a computer having one or more processors and memory storing one or more programs for execution by the one or more processors. The method includes the following actions. At least one blood glucose reading is obtained. A hypoglycemic event is identified when the blood glucose reading meets a hypoglycemic event threshold. A hypo survey associated with the hypoglycemic event is provided. User feedback from the hypo survey is obtained. Then a hypo report including at least a subset of user feedback from the hypo survey is provided.

Another aspect of the disclosure is a method performed on a computer having one or more processors and memory storing one or more programs for execution by the one or more processors. The method includes obtaining user feedback from a hypo survey comprising as follows. Information is provided to display a plurality of hypoglycemic event symptom icon. Then a user selection of one or more of the plurality of the hypoglycemic event symptom icons is recorded. Information is provided to display a plurality of hypoglycemic event cause icons. Then a user selection of one or more of the plurality of hypoglycemic event cause icons is recorded. Information is provided to display a plurality of hypoglycemic event treatment icons. Then a user selection of one or more of the plurality of hypoglycemic event treatment icons is recorded. Finally, a hypo report including at least one symptom icon, at least one cause icon, and at least one treatment icon is provided. It is noted that in some implementations, a user requests a hypo survey because they are feeling hypo, whether or not a hypoglycemic event has been identified.

Thus systems and methods are described that manage and reduce the incidence of hypoglycemia.

BRIEF DESCRIPTION OF THE DRAWINGS

For a better understanding of the aforementioned aspects of the invention as well as additional aspects and implementations thereof, reference should be made to the Description of Implementations below, in conjunction with the following drawings in which like reference numerals refer to corresponding parts throughout the figures.

Like reference numerals refer to corresponding parts throughout the drawings.

DESCRIPTION OF IMPLEMENTATIONS

Reference will now be made in detail to implementations, examples of which are illustrated in the accompanying drawings. In the following detailed description, numerous specific details are set forth in order to provide a thorough understanding of the present implementations. However, it will be apparent to one of ordinary skill in the art that the present various implementations may be practiced without these specific details. In other instances, well-known methods, procedures, components, and networks have not been described in detail so as not to unnecessarily obscure aspects of the implementations.

Figure 1:
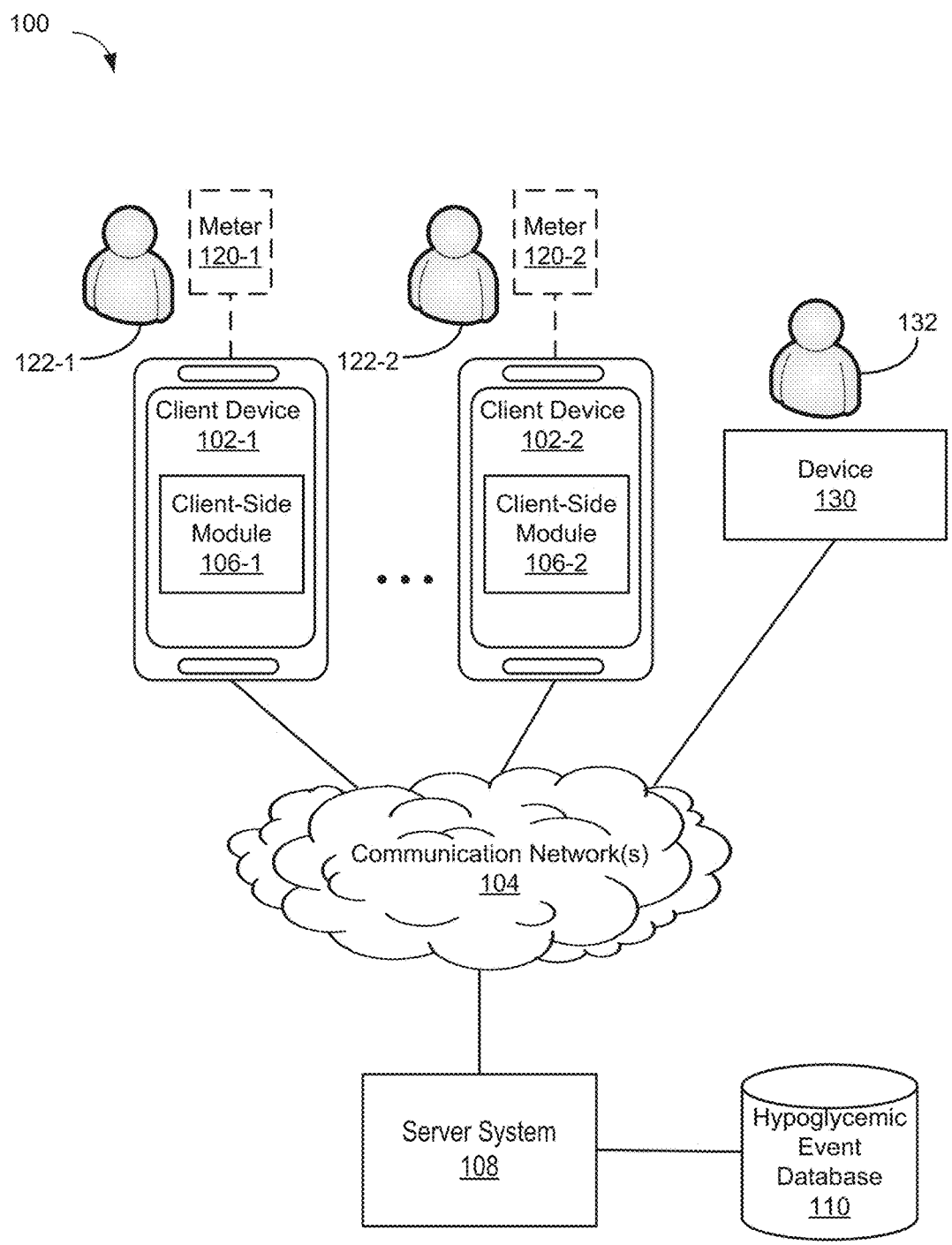
FIG. 1 is a block diagram illustrating a hypoglycemic event management system in accordance with some implementations.

FIG. 1 is a block diagram illustrating a computer system 100 that provides hypoglycemic event management in accordance with some implementations. In some implementations, the computer system 100 includes client-side modules (or "module") 106-1, 106-2 . . . executed on client devices 102-1, 102-2 . . . , at least one computing user device 130, and a server system 108 coupled to a hypoglycemic event database 110. The client-side modules 106 communicate with the server 108 and/or the device 130 and/or the hypoglycemic event database 110 through one or more communication networks 104. The client-side modules 106 provide hypoglycemic event data collection, analysis, and presentation functionality and communicate with the server 108. The client-side modules 106 are described in further details below with respect to FIG. 2. The server 108 provides server-side functionality (e.g., analysis and handling requests to read/write data) for any number of client-side modules 106, each residing on a respective client device 102.

In some implementations, the client devices 102 are computing devices such as desktop computers, laptop computers, tablet computers, smart phones, and other mobile devices. Patients 122 can edit or enter hypoglycemic event data including blood glucose readings in addition to viewing hypoglycemic event analysis. In some implementations, the patients 122 can connect meters 120 to their devices to obtain blood glucose readings stored on the meters 120. Various meters 120 known in the art can be used by the patients 122 to manually, automatically, or periodically obtain blood glucose readings. The obtained readings are stored at the device and synchronized between the client device 102 and the meter 120. Although FIG. 1 shows one meter 120 connected to each client device 102, in some implementations, more than one meter 120 can be connected to each client device 102 in order to obtain readings. Wired or wireless connections can be used to transmit the readings to a client device 102 for hypoglycemic event analysis. Other methods of entering the hypoglycemic event data into a client device 102 include manual entry and/or downloading from other computing devices or systems. These methods can be used in place of or in addition to syncing a client device with a meter 120.

Upon receiving the readings, client-side modules 106 residing on the client devices 102 capture hypoglycemic event data as described herein. In some implementations, the client-side modules 106 further perform analysis of the hypoglycemic event data including the blood glucose readings, and present the analysis to the user 122.

In some implementations, the client device 102 transmits the data to a server system 108 via communication network(s) 104. The data received by the server 108 is the stored in the hypoglycemic event database 110 in accordance with some implementations.

In some implementations, the server 108 includes one or more processors, and one or more databases. In some implementations, the server provides a web interface to one or more client side devices. The web interface to one or more client side devices facilitates the processing of input and output associated with the client side devices for one or more server-side modules. The one or more processors obtain hypoglycemic event data, analyze the data, and transmit the analysis result to the client devices 102 upon request. The hypoglycemic event database 110 stores various information, such as user profiles and hypoglycemic event data. Although FIG. 1 shows the hypoglycemic event database 110 as a separate database from the server 108, the hypoglycemic event database 110 is implemented by the server 108 in some implementations.

In addition to the client devices 102 used by the patients 122, computing device 130 can be used by others to access the data as well. In some instances, other people 132 such as doctors, nurses, or medical insurance company personnel are authorized to view hypoglycemic event data. These other people 132 are sometimes referred to as providers (e.g., doctors and nurses) and payers (e.g., the insurance companies). Modules residing on the device 130 can request data from the server 108. In response, the server 108 retrieves data from the client devices 102 or the hypoglycemic event database 110, and transmits the result to the device 130. Examples of a device 130 include a handheld computer, a wearable computing device, a personal digital assistant (PDA), a tablet computer, a laptop computer, a cellular telephone, a smart phone, an enhanced general packet radio service (EGPRS) mobile phone, a media player, a navigation device, a portable gaming device console, a desktop computer, or a combination of any two or more of these data processing devices or other data processing devices.

In FIG. 1, the client devices 102, the device 130, and the server 108 are connected to the communication network(s) 104. The communication network(s) 104 can be any wired or wireless local area network (LAN) and/or wide area network (WAN), such as an intranet, an extranet, or the Internet. It is sufficient that the communication network 140 provides communication capability between the client devices 102, the device 130, and the server.

The computer system 100 illustrated in FIG. 1 includes both a client-side portion (e.g., the client devices 102 and/or the device 130) and a server-side portion (e.g., the server 108). In some implementations, hypoglycemic event data processing is implemented entirely on a client device 102 or the device 130. In some implementations, the division of functionality between the client device 102 and server portions of hypoglycemic event data processing vary (e.g., configurable for individual patients 122 or specific device types). For example, in some implementations, the client-side modules 106 are thin-clients that provide hypoglycemic event data entry and output report functions, and delegate other data processing functionalities to a backend server (e.g., the server system 108).

Figure 2:
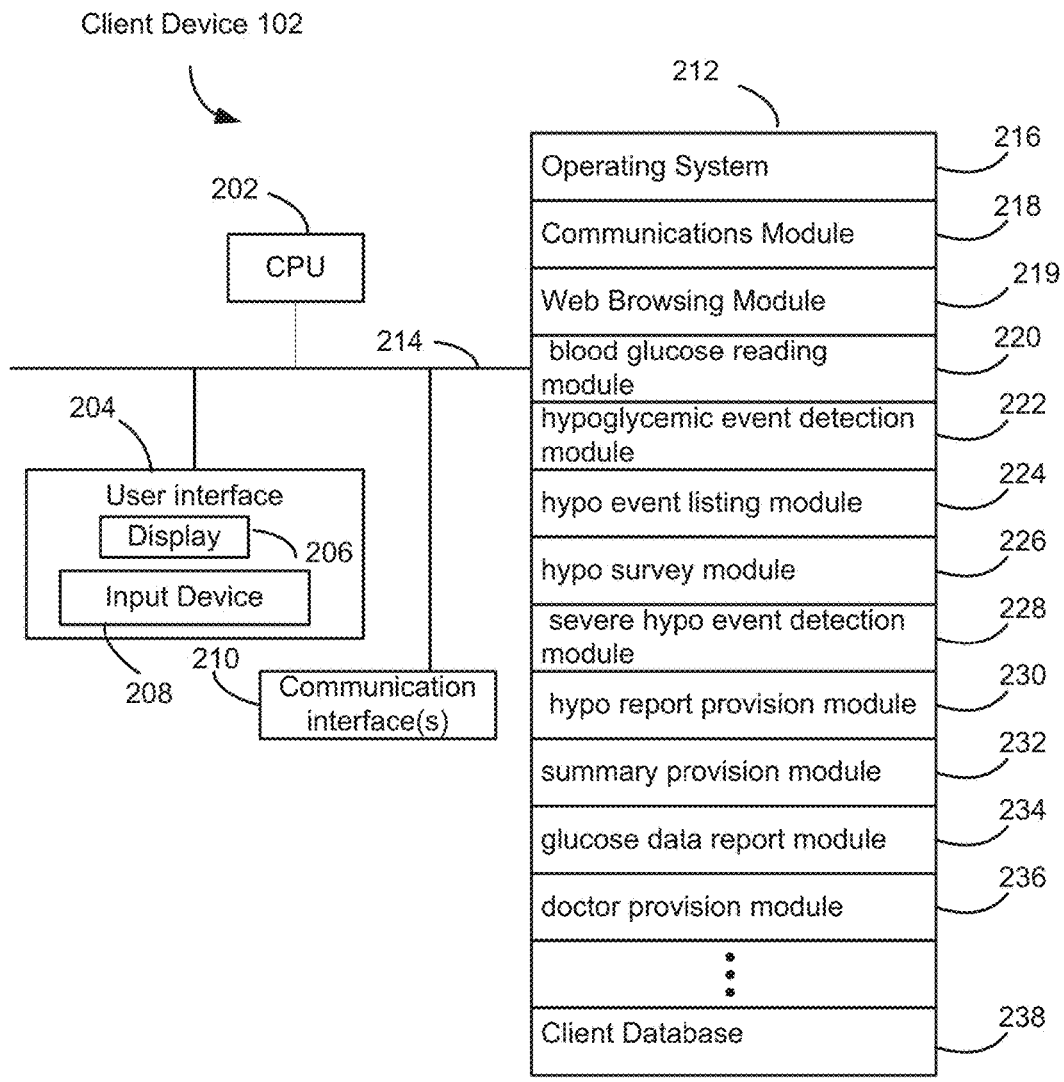
FIG. 2 is an exemplary client device used in the hypoglycemic event management system in accordance with some implementations.
Figures 5A, 5B:
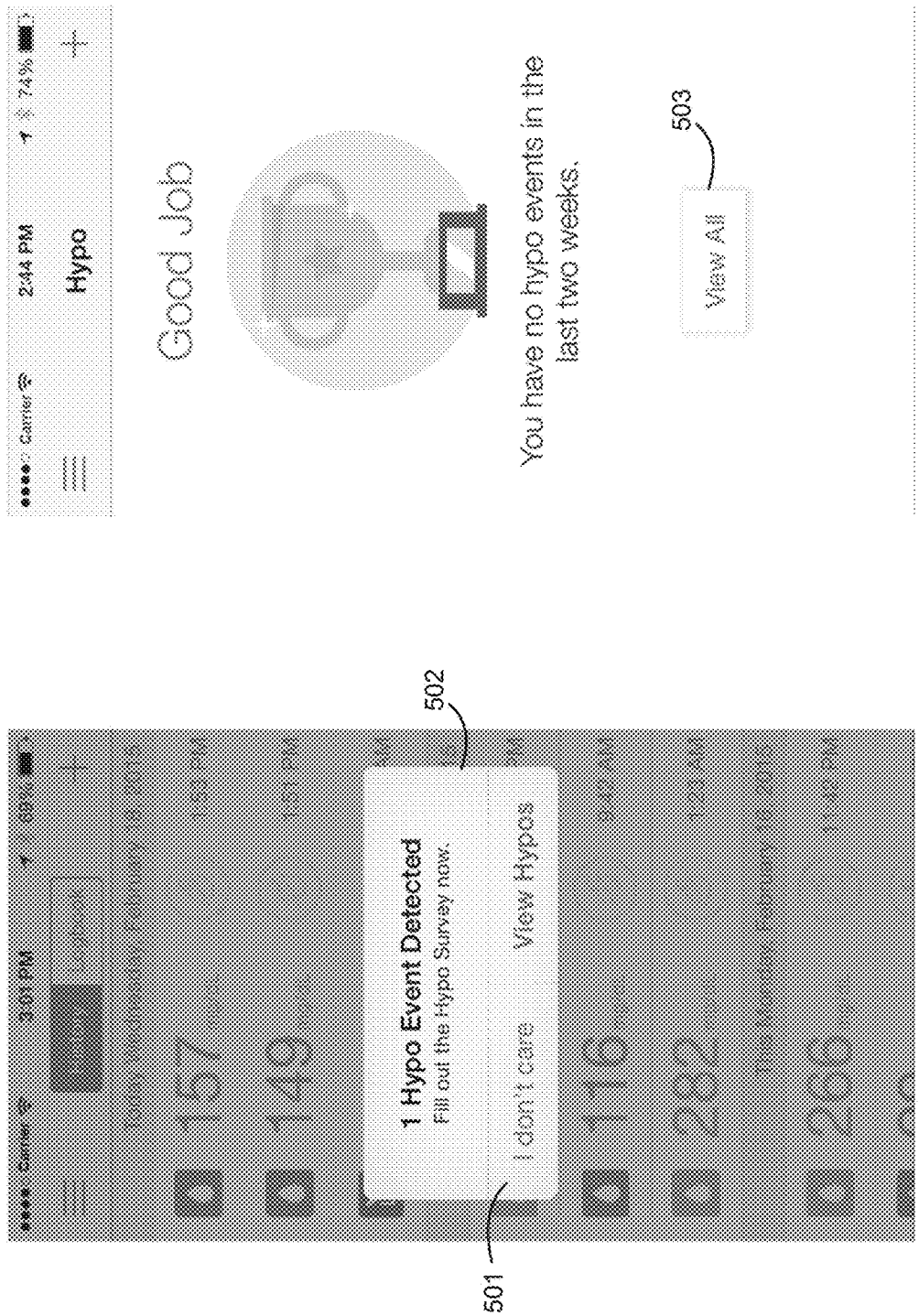
FIG. 5A is a screen shot of at least one hypo event detection, in accordance with some implementations.
FIG. 5B is a screen shot of no hypo event detection, in accordance with some implementations.
Figure 5C:
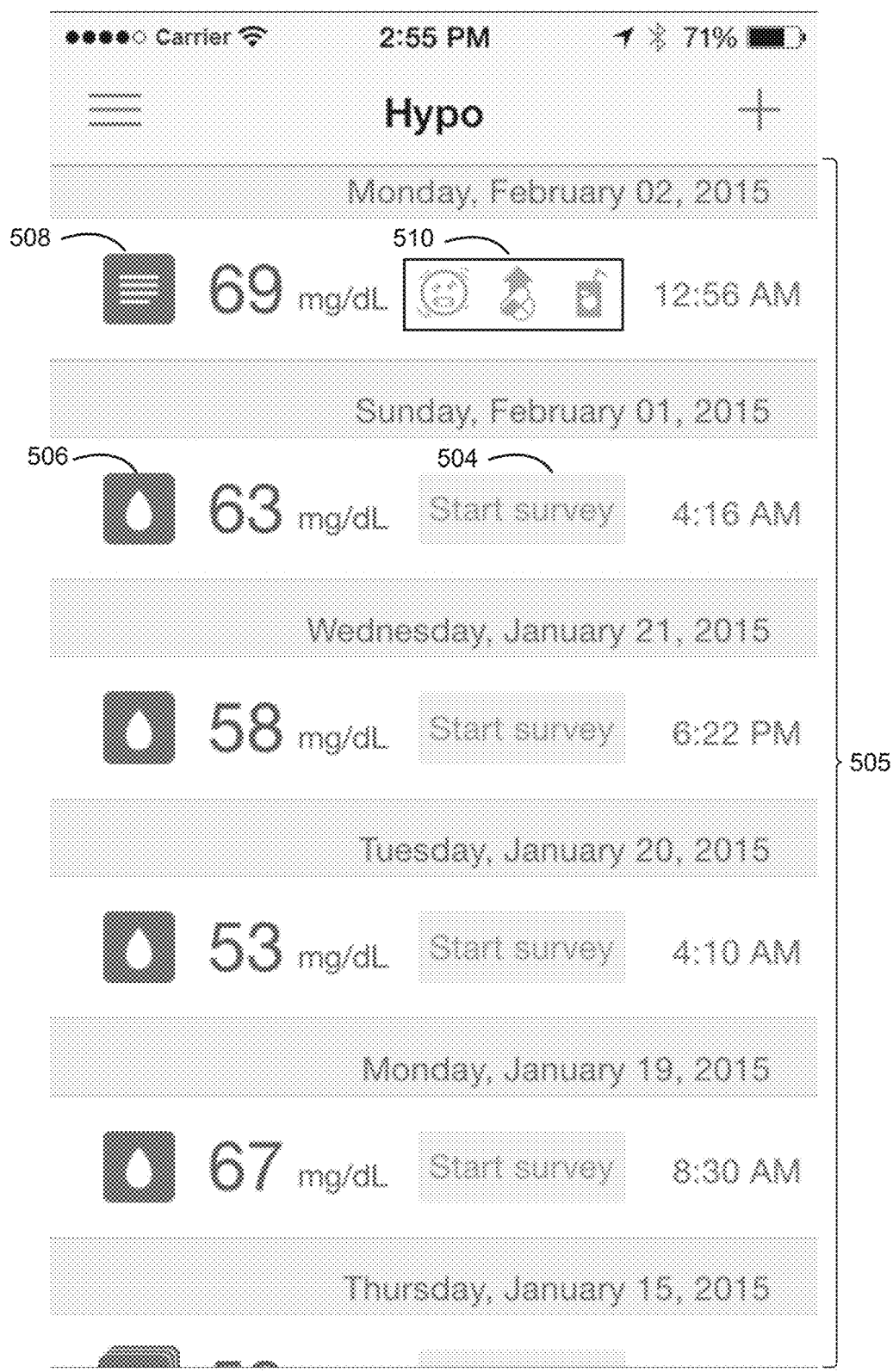
FIG. 5C is a screen shot of a list of hypo events, in accordance with some implementations.
Figure 5D:
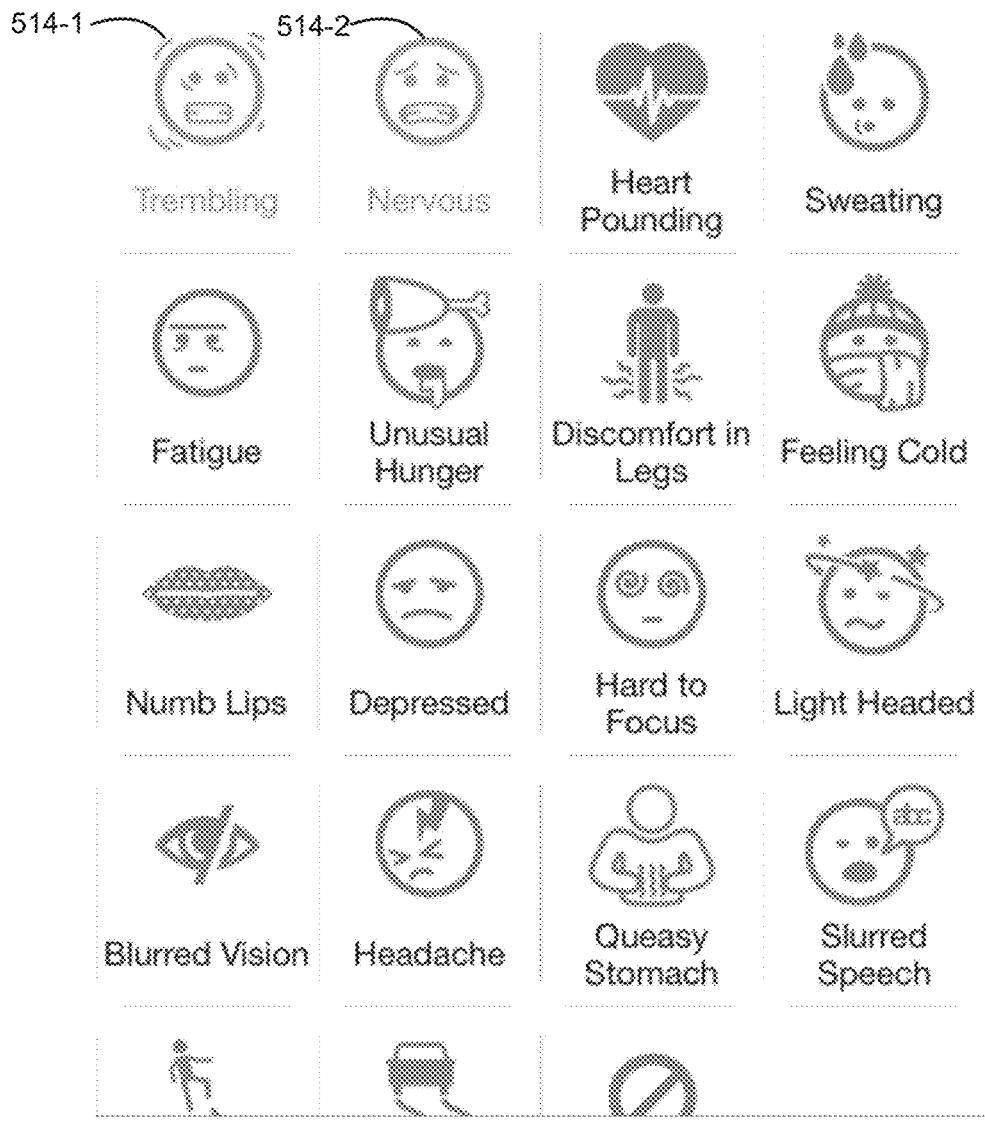
FIG. 5D is a screen shot of a hypo survey for obtaining symptoms feedback, in accordance with some implementations.
Figure 5E:
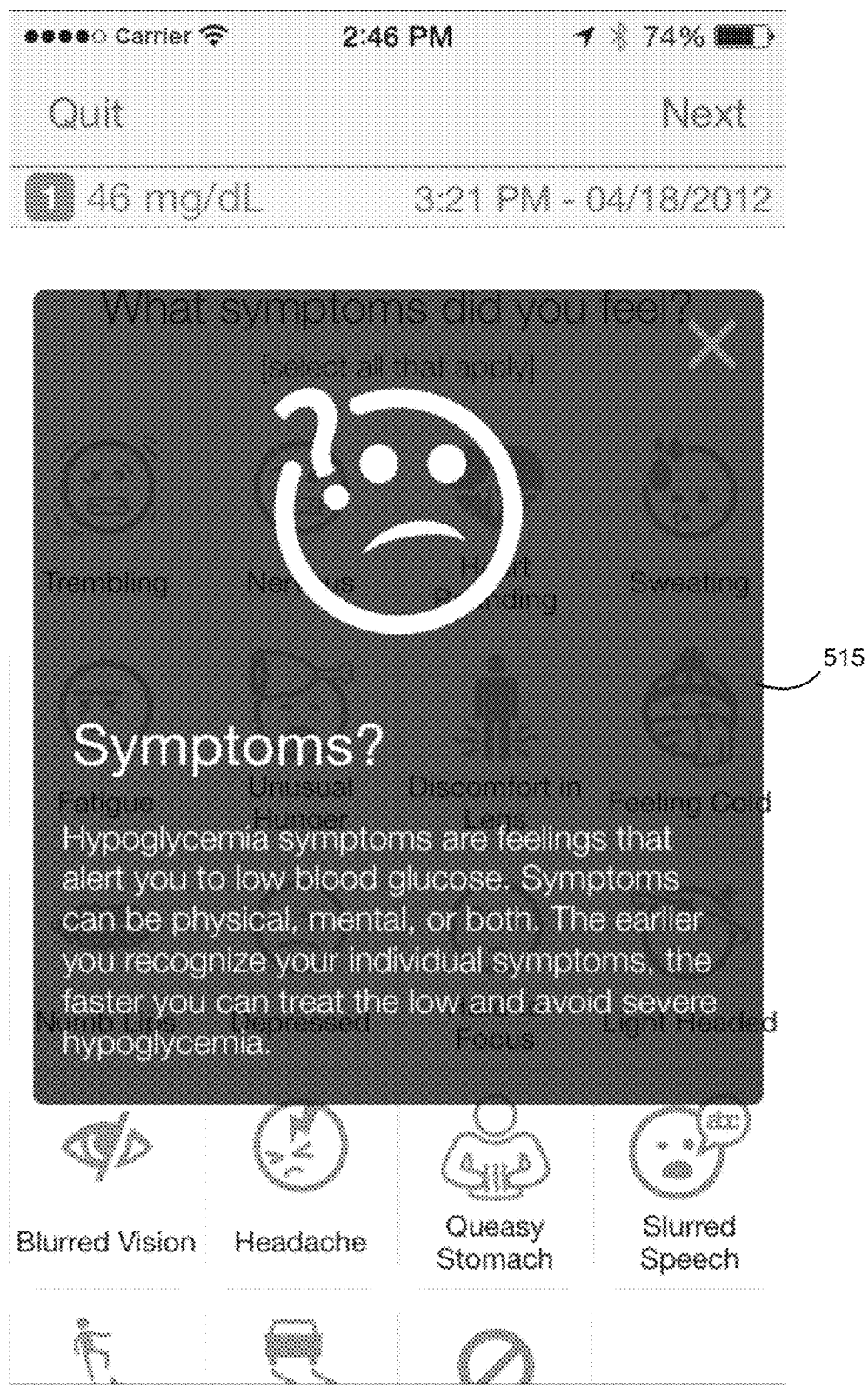
FIG. 5E is another screen shot of a hypo survey for obtaining symptoms feedback including an instructive tool tip, in accordance with some implementations.
Figure 5F:
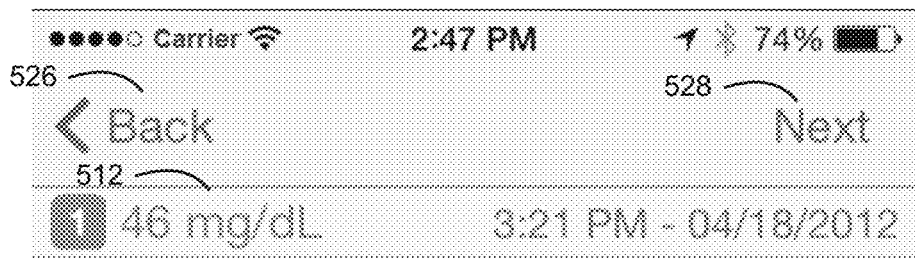
FIG. 5F is a screen shot of a hypo survey for obtaining causes feedback, in accordance with some implementations.
Figure 5F:
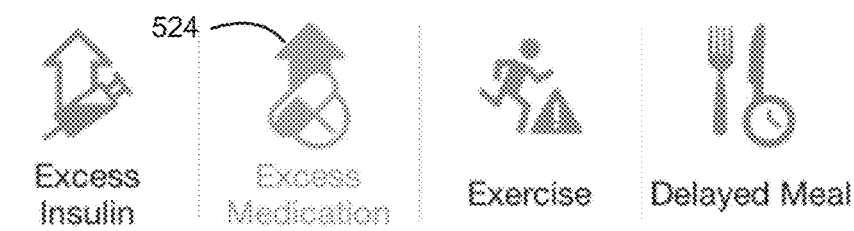
Figure 5F:
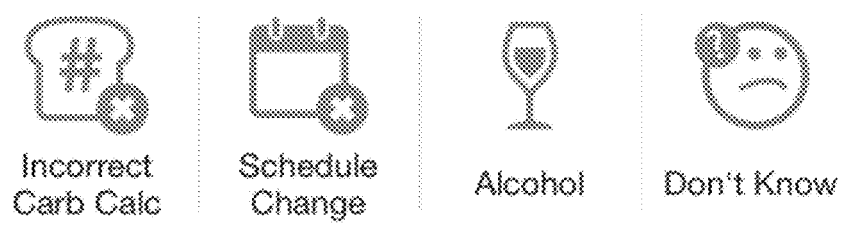
Figure 5F:
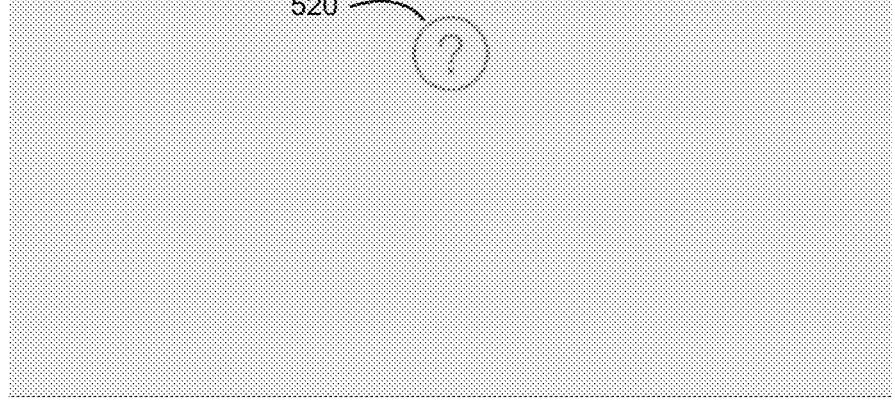
Figure 5G:
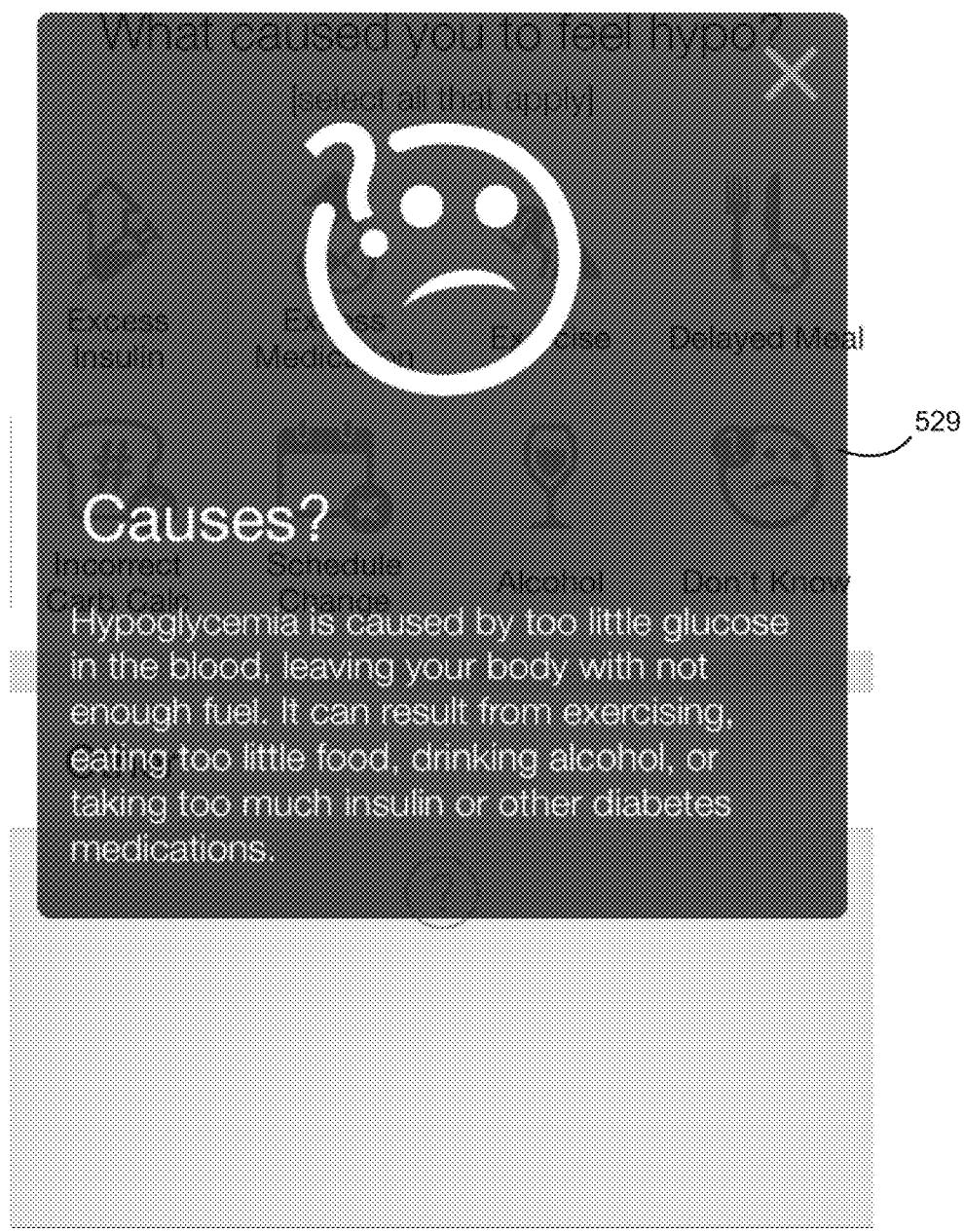
FIG. 5G is a screen shot of a hypo survey for obtaining causes feedback including an instructive tool tip, in accordance with some implementations.
Figure 5H:
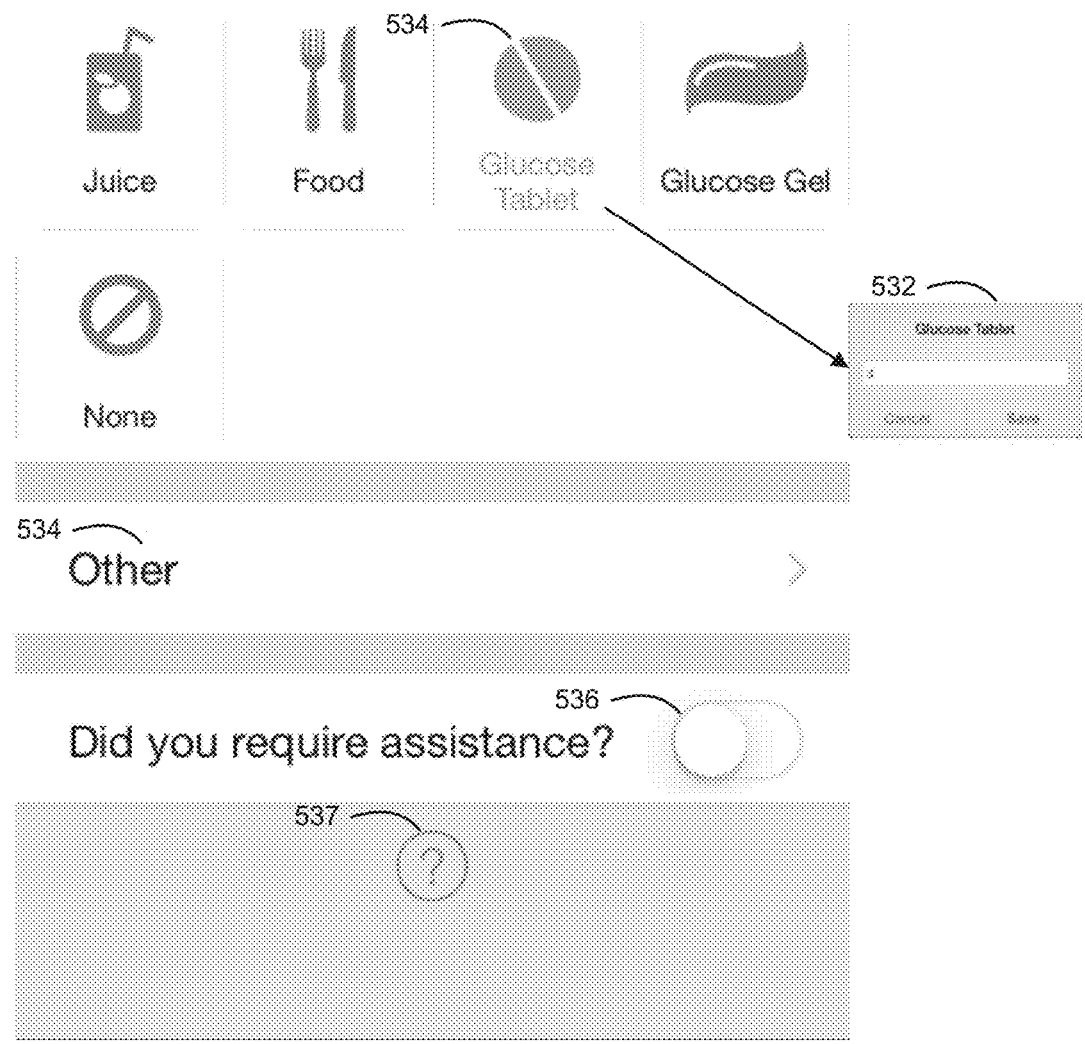
FIG. 5H is a screen shot of a hypo survey for obtaining treatment feedback, in accordance with some implementations.
Figure 5I:
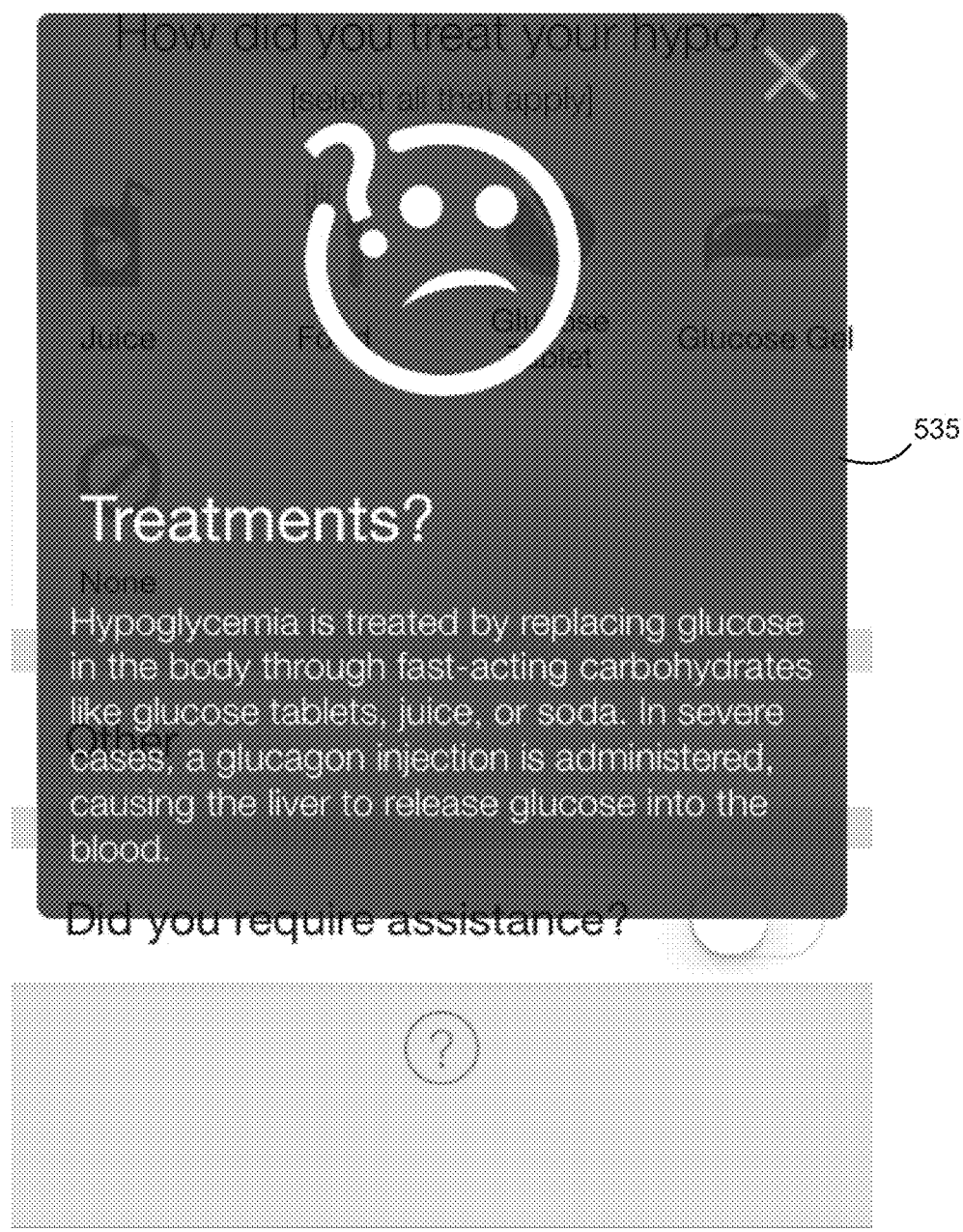
FIG. 5I is another screen shot of a hypo survey for obtaining treatment feedback including an instructive tool tip, in accordance with some implementations.
Figure 5J:
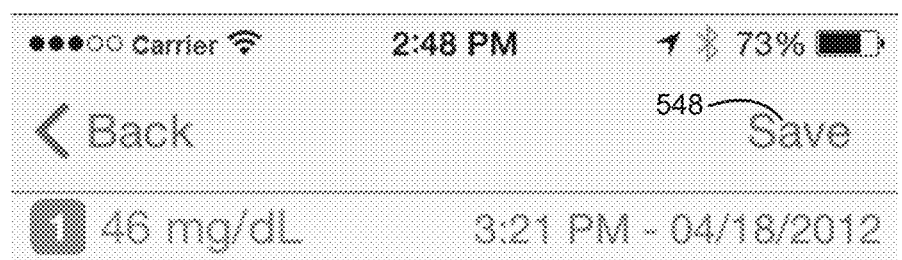
FIG. 5J is a screen shot of a hypo summary, in accordance with some implementations.
Figure 5J:
Figure 5J:
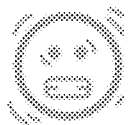
Figure 5J:
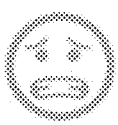
Figure 5J:
Figure 5J:
Figure 5J:
Figure 5J:
Figure 5K:
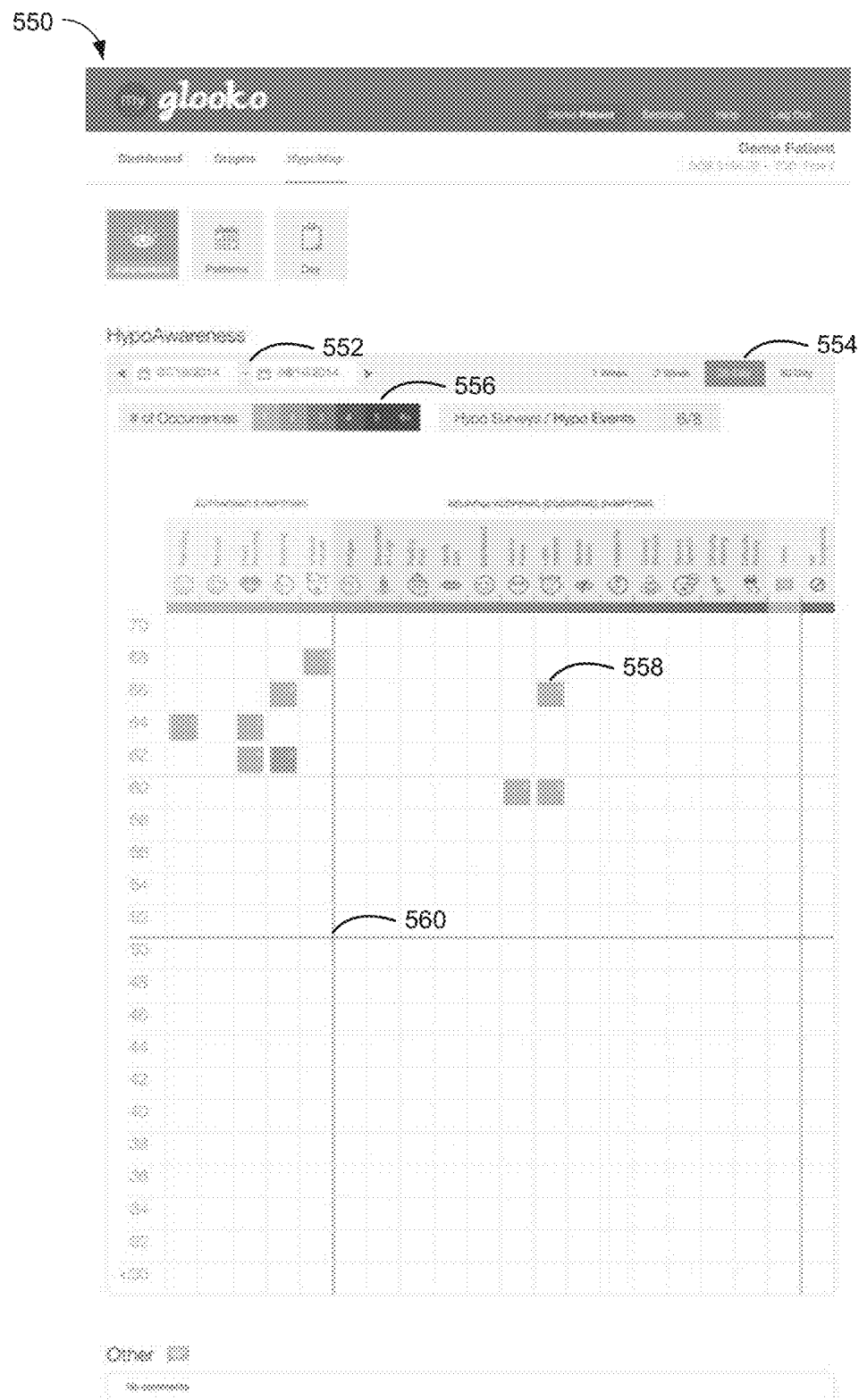
FIG. 5K is a screen shot of a hypo awareness grid, in accordance with some implementations.
Figure 5L:
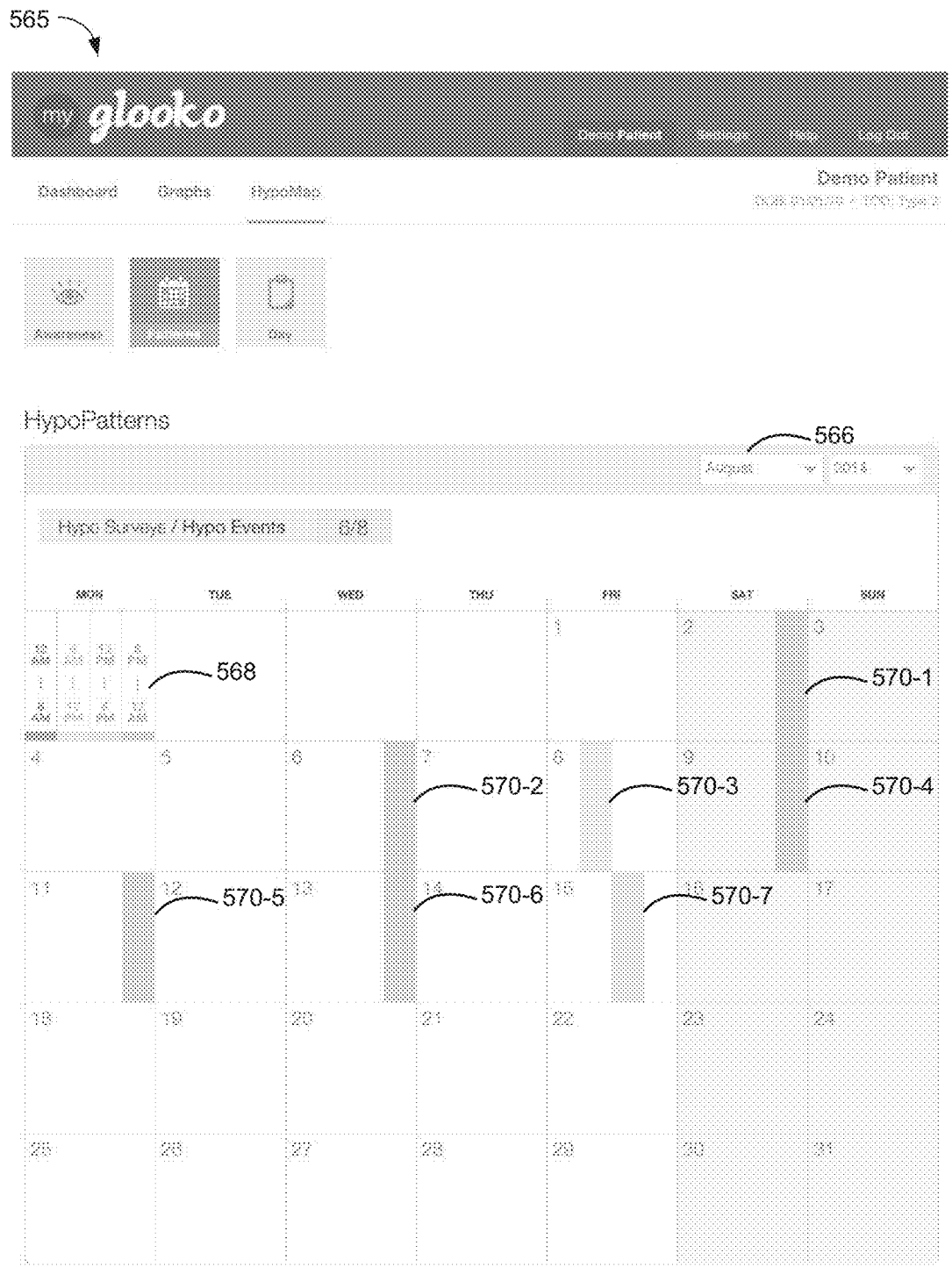
FIG. 5L is a screen shot of a hypo pattern report, in accordance with some implementations.
Figure 5M:
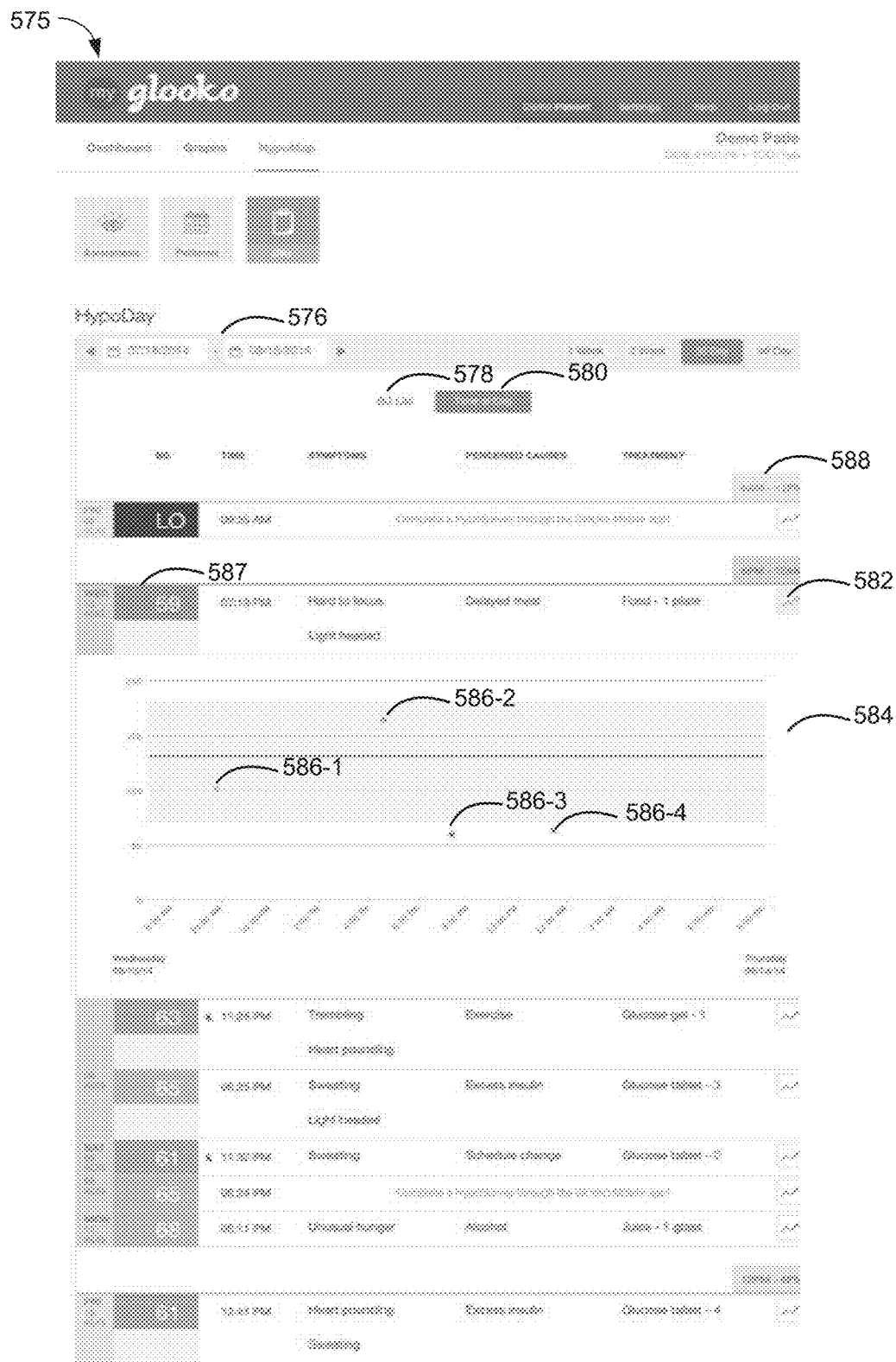
FIG. 5M is a screen shot of a hypo day report, in accordance with some implementations.
Figure 6A:
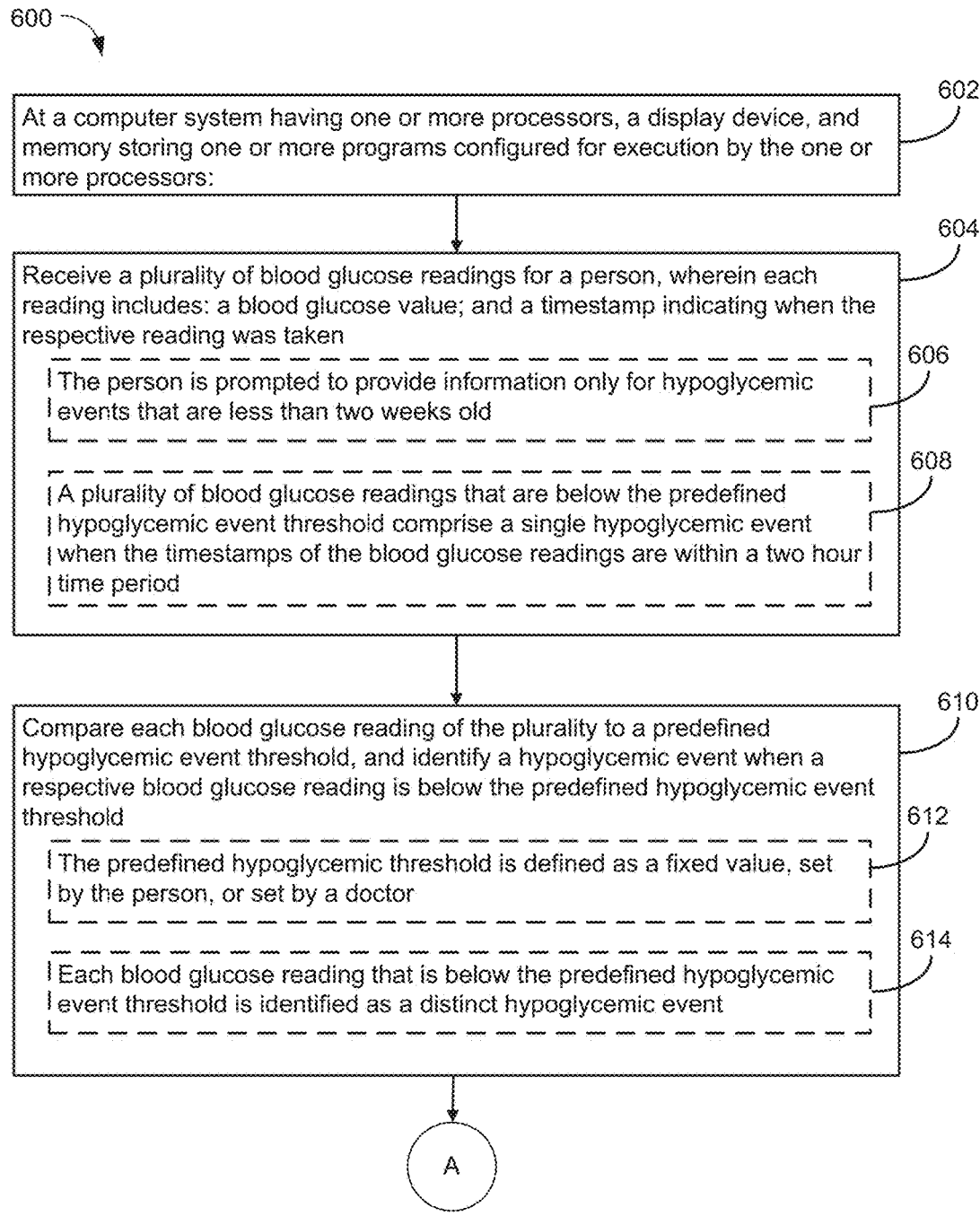
FIGS. 6A-6F illustrate a flowchart representing a method of receiving hypoglycemic event data, analyzing the data, and providing reports based on the data, in accordance with some implementations.
Figure 6B:
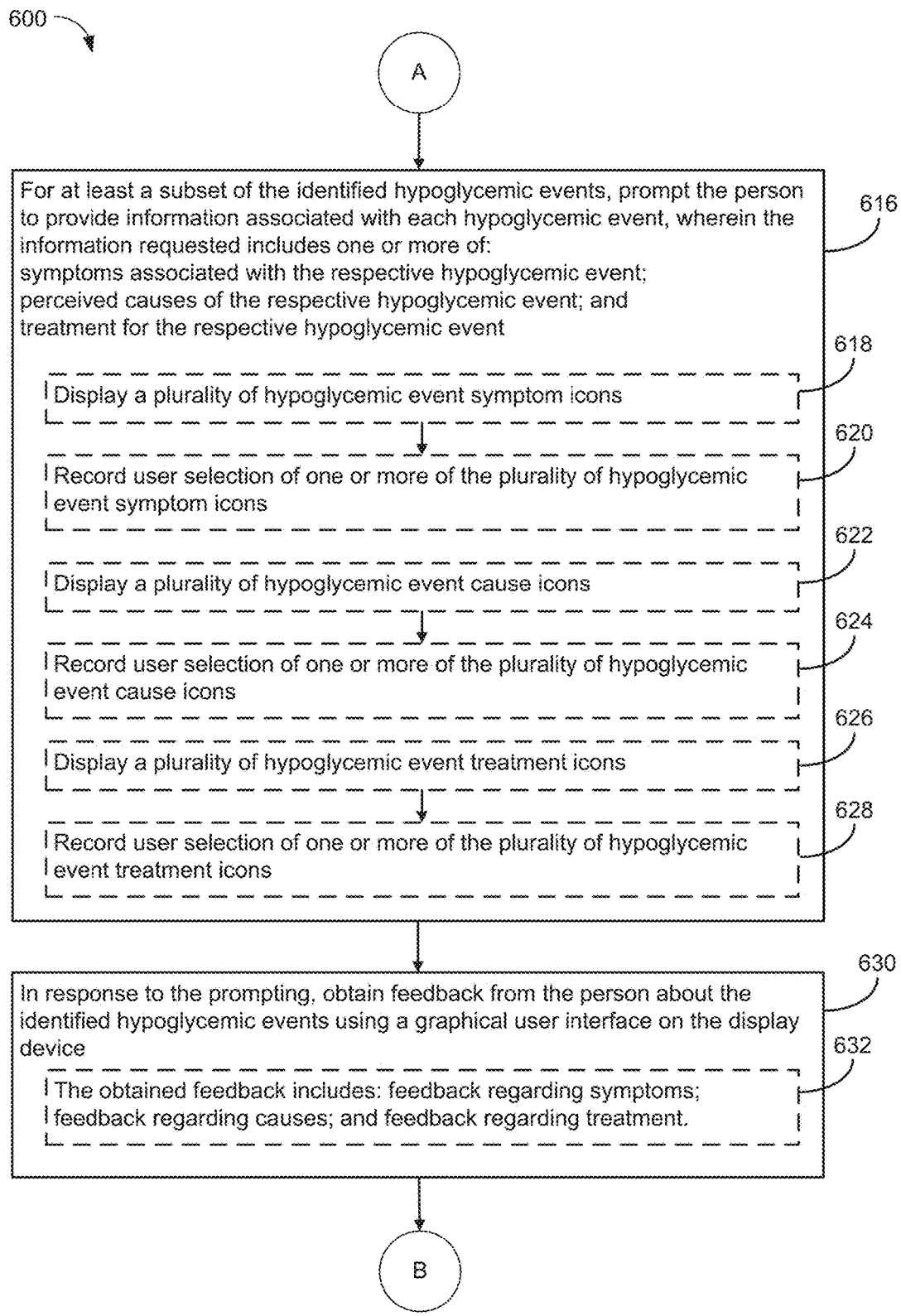
Figure 6C:
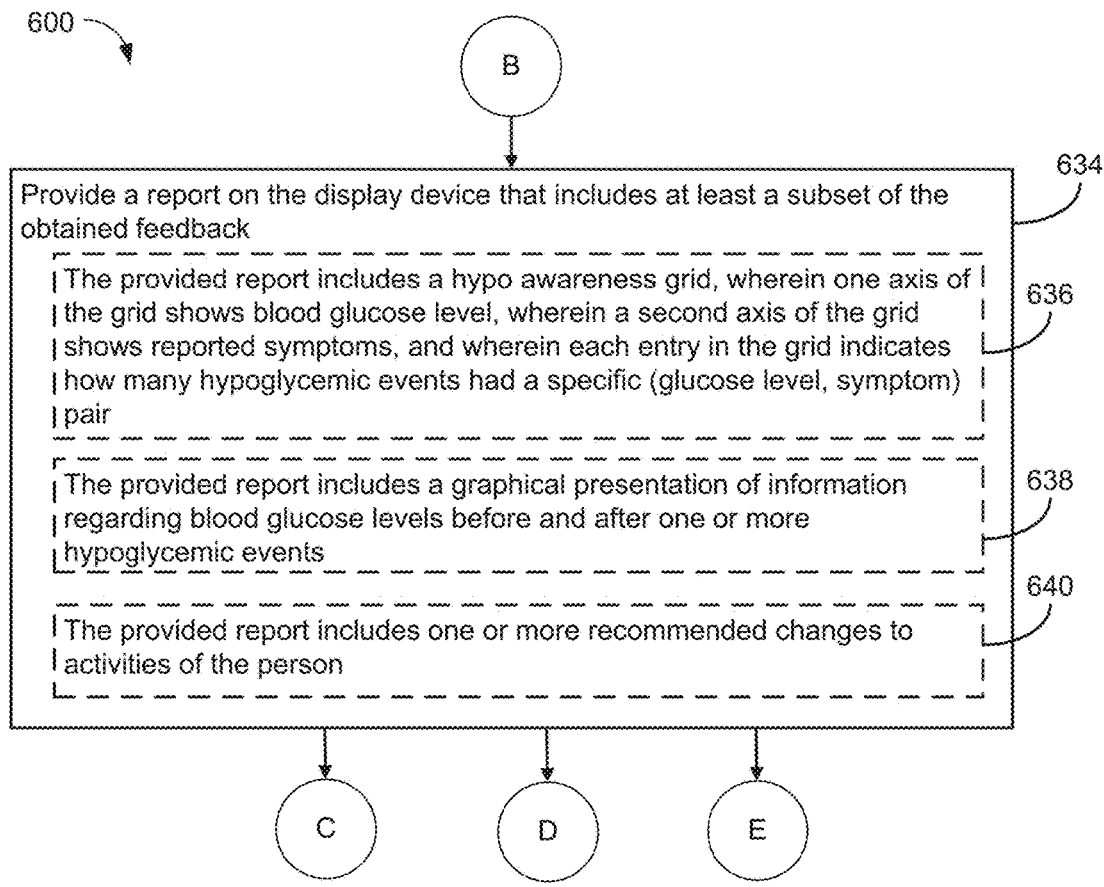
Figure 6D:
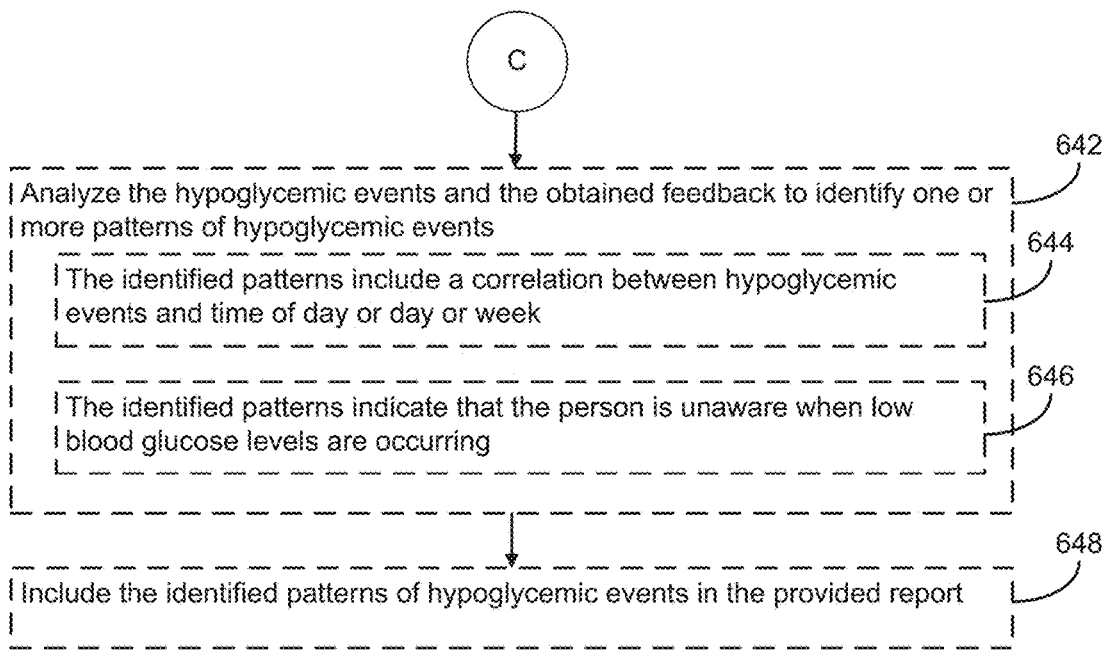
Figure 6E:
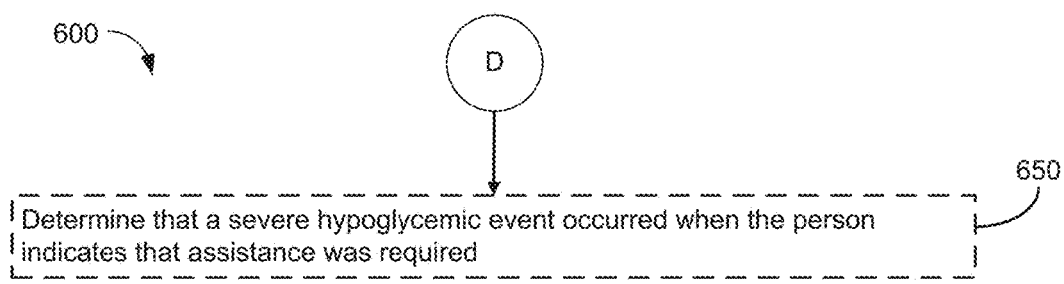
Figure 6F:
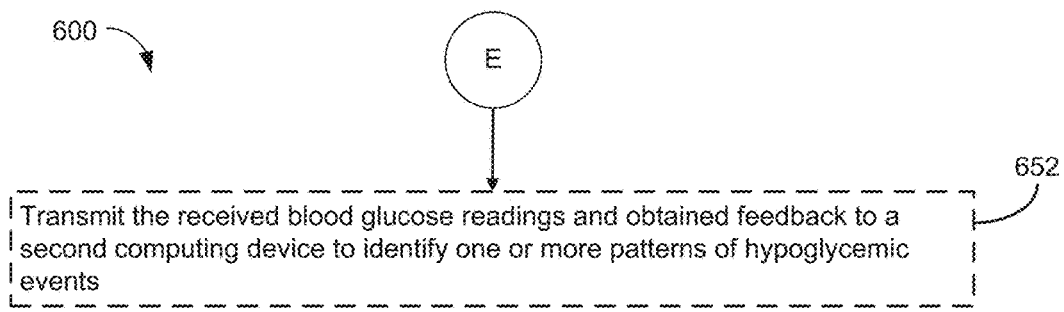

FIG. 2 is a block diagram illustrating the client device 102 in accordance with some implementations. The client device 102 typically includes one or more processing units (CPU's) 202, one or more network or other communications interfaces 210, memory 212, and one or more communication buses 214 for interconnecting these components. The communication buses 214 optionally include circuitry (sometimes called a chipset) that interconnects and controls communications between system components. The computer 200 includes a user interface 204 comprising a display device 206 and one or more input device(s) 208, such as a keyboard, a mouse, touch sensitive display screen, or other pointing device. Memory 212 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 212 optionally includes one or more storage devices remotely located from the CPU(s) 202. Memory 212, or alternately the non-volatile memory device(s) within memory 212, comprises a non-transitory computer readable storage medium. In some implementations, memory 212 or the computer readable storage medium of memory 212 stores the following programs, modules and data structures, or a subset thereof:

- an operating system 216 that includes procedures for handling various basic system services and for performing hardware dependent tasks;
- a network communication module 218 that is used for connecting the computer 200 to other computers via the one or more communication network interfaces 210 (wired or wireless) and one or more communication networks 104, such as the Internet, other wide area networks, local area networks, metropolitan area networks, and so on;
- a web browsing module 219, which enables a user to communicate over a network 108 (such as the Internet) with remote computers or devices;
- a blood glucose reading module 220 for receiving any number of blood glucose readings;
- a hypoglycemic event detection module 222 for identifying hypoglycemic events that include one or more blood glucose readings that reach the threshold (e.g. below 70 mg/dL);
- a hypo event listing module 224 which displays a listing of one or more hypoglycemic events, as illustrated in FIG. 5C below;
- a hypo survey module 226, which prompts a user to provide information about symptoms, causes, and treatment for hypoglycemic events, as illustrated below in FIGS. 5D-5J;
- a severe hypo event detection module 228 for detecting severe hypo events based on survey feedback. Sever hypo events are typically those hypo events where the treatment require assistance of others;
- a hypo report provision module 230 for providing a short report of at least a subset of the user feedback for a plurality of hypo events, typically during a span of time such as two weeks;
- a summary provision module 232 where the summary includes all, or almost all, of the feedback information obtained from the user for an individual hypo event, as illustrated in FIG. 5J;
- a glucose data report module 234 for producing various reports such as a hypo awareness grid and/or hypo overview report, as illustrated in FIGS. 5K, 5L, and 5M;
- a doctor provision module 236 for providing information from hypo events to a doctor, including both the blood glucose readings as well as the feedback provided by the user regarding symptoms, causes, and treatment; and
- a client database 238 for storing hypoglycemic event data including but not limited to blood glucose readings received by the blood glucose reading module 220, hypoglycemic survey data collected by the hypoglycemic survey module 226, among others.

Each of the above identified elements is typically stored in one or more of the previously mentioned memory devices, and corresponds to a set of instructions for performing a function described above. The above identified modules or programs (i.e., sets of instructions) need not be implemented as separate software programs, procedures or modules, and thus various subsets of these modules may be combined or otherwise re-arranged in various implementations. In some implementations, memory 212 stores a subset of the modules and data structures identified above. Furthermore, memory 212 may store additional modules and data structures not described above.

Although FIG. 2 shows a client device, FIG. 2 is intended more as functional description of various features that may be present in a client device than as a structural schematic of the implementations described herein. In practice, and as recognized by those of ordinary skill in the art, items shown separately could be combined and some items could be separated. For example, some items shown separately in FIG. 2 could be implemented on the client 102 or portions could be implemented on the server system 108. Furthermore, the actual number of modules and how features are allocated among them can vary from one implementation to another.

Figure 3:
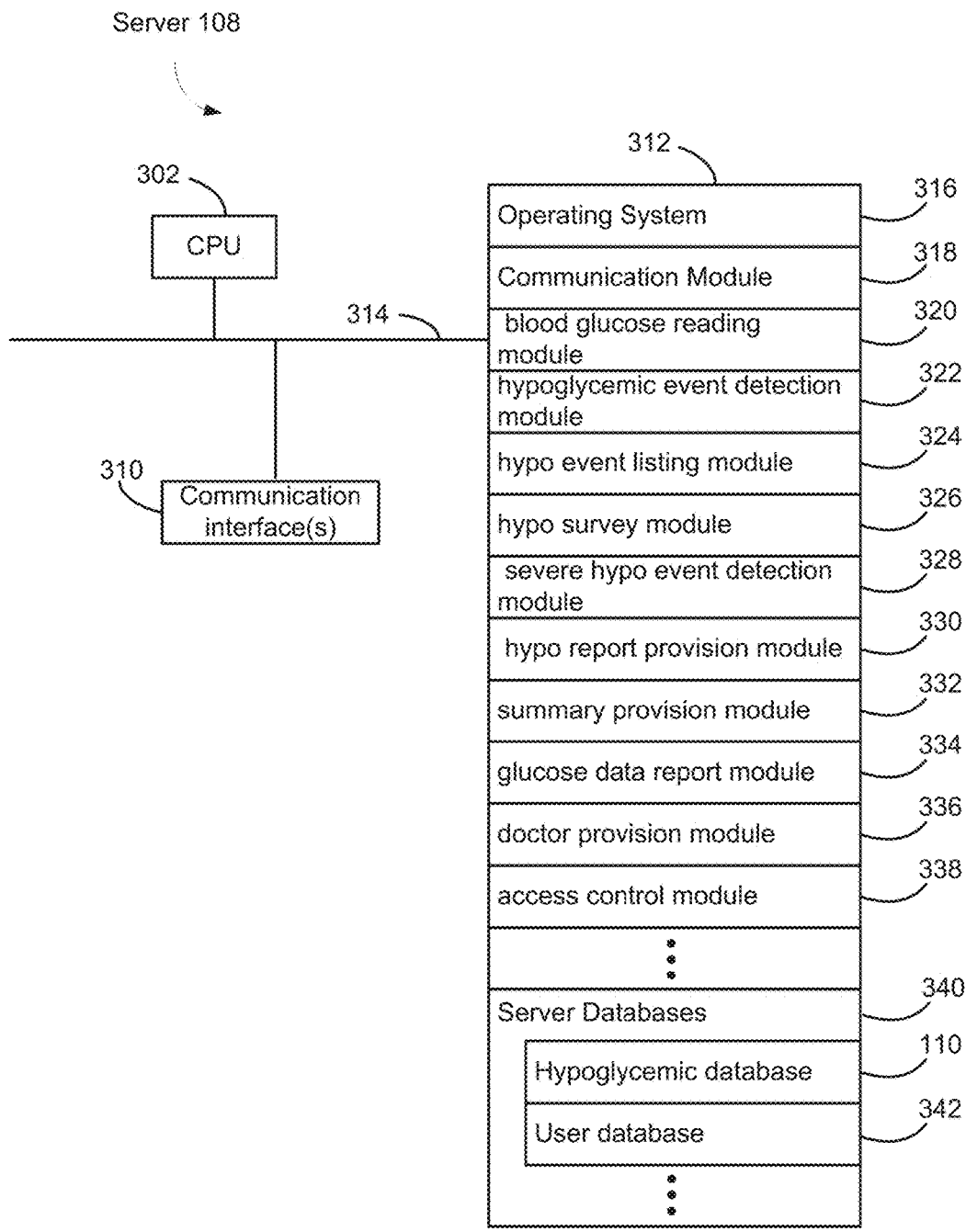
FIG. 3 is an exemplary server system used in the hypoglycemic event management system in accordance with some implementations.

FIG. 3 is a block diagram illustrating the server system 108 in accordance with some implementations. The server system 108 may include one or more processing units (e.g., CPUs and/or GPUs) 302, one or more network interfaces 310, one or more memory units 312, and one or more communication buses 314 for interconnecting these components (e.g. a chipset).

The memory 312 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 312, optionally, includes one or more storage devices remotely located from one or more processing units 302. The memory 312, or alternatively the non-volatile memory within the memory 312, includes a non-transitory computer readable storage medium. In some implementations, the memory 312, or the non-transitory computer readable storage medium of the memory 312, stores the following programs, modules, and data structures, or a subset or superset thereof:

- operating system 316 including procedures for handling various basic system services and for performing hardware dependent tasks;
- network communication module 318 for connecting server system 108 to other computing devices (e.g., the client devices 102 or devices 130) connected to one or more networks 104);
- a blood glucose reading module 320 for receiving any number of blood glucose readings;
- a hypoglycemic event detection module 322 for identifying hypoglycemic events that include one or more blood glucose readings that reach the predefined hypoglycemic event threshold (e.g. below 70 mg/dL);
- a hypo event listing module 324 which displays a listing of one or more hypoglycemic events, as illustrated below in FIG. 5C;
- a hypo survey module 326, as described above with respect to the hypo survey module 226 on a client device 102;
- a severe hypo event detection module 328 for detecting severe hypo events based on survey feedback;
- a hypo report provision module 330 for providing a short report of at least a subset of the user feedback, as described above with respect to the hypo survey module 226 on a client device 102;
- a summary provision module 332 where the summary includes all, or almost all of the feedback information provided, as described above with respect to the summary provision module 232 on a client device 102;
- a glucose data report module 334 for producing various reports such as a hypo awareness grid and/or hypo overview report;
- a doctor provision module 336 for providing at least some information from the hypo report to a doctor;
- an access control module 338 for authentication and authorization of requests to view hypoglycemic data for a patient 122. The access control module 338 limits access to those individuals who are authorized (e.g., the patient herself or the personal physician); and
- one or more server databases 340 for storing hypoglycemic event data, including:
    - the hypoglycemic database 110 for storing hypoglycemic event data including blood glucose readings and hypoglycemic survey data. In some implementations, the blood glucose readings and survey data are received from a client device; and
    - a user database 342 for storing user profiles and other user data. In some implementations, the access control module 338 uses the user database 342 for authentication and authorization.

As illustrated above, the functionality described in FIGS. 2 and 3 may be implemented on either a client device 102, a server 108, or both. Various implementations allocate functionality between a client device 102 and a server 108 in various ways. In some implementations, the allocation of functionality is configurable based on individual devices. For example, a patient 122 who primarily uses a small mobile device may use the mobile device for entering survey data, but may use a desktop computer or laptop computer to access a web application provided by the server 108. In another case, a single device (such as a desktop computer, a laptop computer, or a tablet computer) may perform all of the functions described above, without transmitting the data to a server. In some implementations, data may be transmitted to a server 108 just so that it will be accessible by others, such as doctors and nurses.

In some implementations, the modules 320-326 are provided as part of a web application, which can be accessed by a web browser 219 on a client device 102 or device 130.

Although FIG. 3 shows a server 108, FIG. 3 is intended more as functional description of various features that may be present in system with one or more servers rather than as a structural schematic of the implementations described herein. In practice, and as recognized by those of ordinary skill in the art, items shown separately could be combined and some items could be separated. Furthermore, the actual number of modules and how features are allocated among them can vary from one implementation to another.

Figure 4:
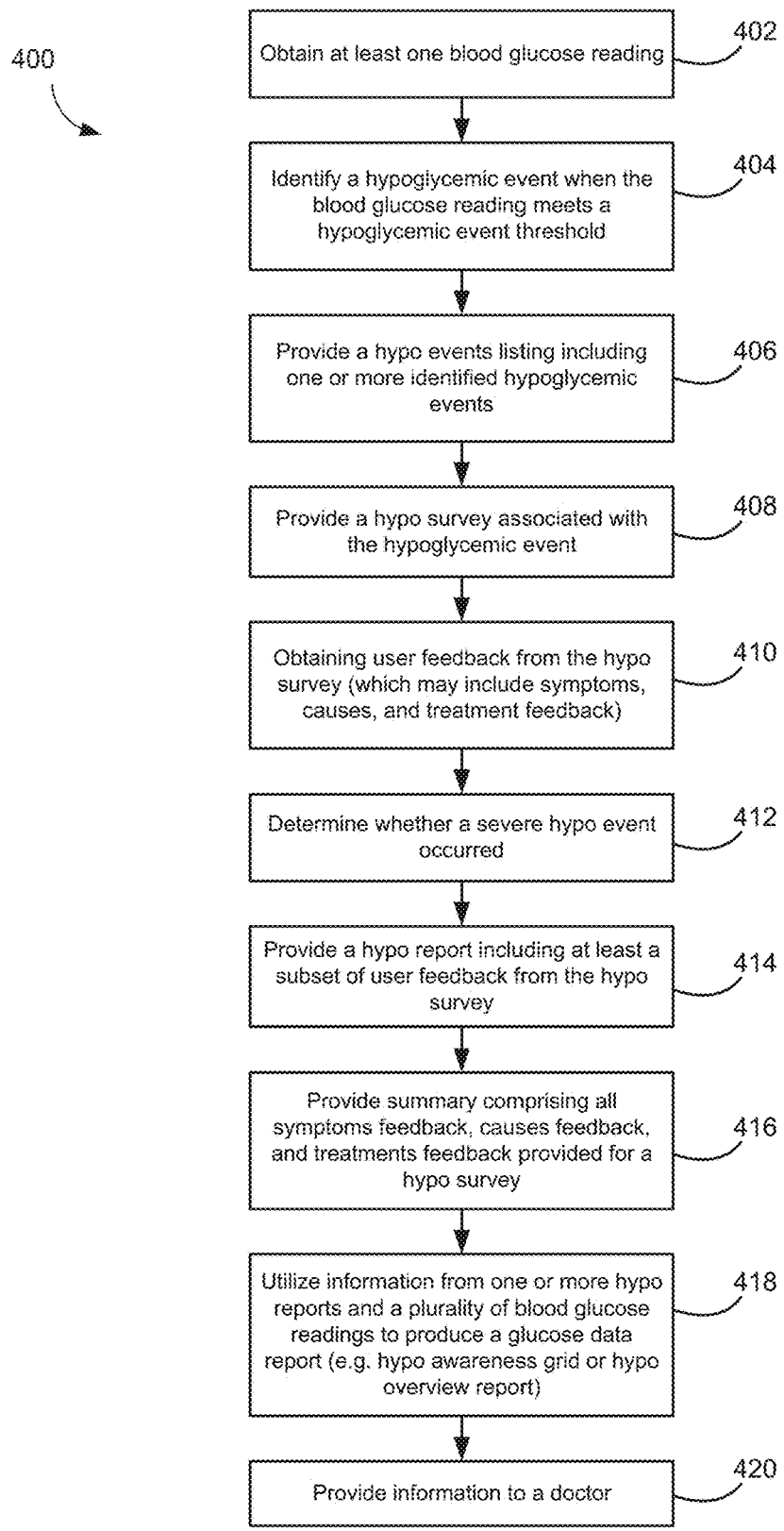
FIG. 4 is a flowchart representing a method of capturing hypoglycemic event data, analyzing the data, and producing reports based on the data in accordance with some implementations.

FIG. 4 is a flowchart representing a method 400 for capturing hypoglycemic event data, according to some implementations. In some implementations, the method 400 is governed by instructions that are stored on a computer readable storage medium. The instructions are executed by one or more processors. Each of the operations shown in FIG. 4 typically corresponds to instructions stored in a computer memory or non-transitory computer readable storage medium. The computer readable storage medium typically includes a magnetic or optical disk storage device, solid state storage devices such as Flash memory, or other non-volatile memory device or devices. The computer readable instructions stored on the computer readable storage medium are in source code, assembly language code, object code, or other instruction format that is interpreted by one or more processors. Various operations shown in FIG. 4 correspond to instructions in the modules of the server system 108 shown in FIG. 3 and/or the client device 102 shown in FIG. 2. Some of the processes listed in FIG. 4 are described in more detail with respect to the user interface screens shown in FIGS. 5A-5L.

In some implementations, a client device 102 obtains (402) at least one blood glucose reading. In some implementations, the client device 102 can obtain blood glucose readings after the patient 122 connects a meter 120 to the client device 102. Synchronizing the blood glucose readings with the meter 120, the client device 102 obtains the blood glucose readings. In some implementations, the client-side modules 106 on the client devices 102 provide user interfaces to allow additional inputs to each blood glucose reading as part of logging each event.

In some implementations, based on the readings, the client-side modules 106 further identify (404) a hypoglycemic event when the blood glucose reading meets a hypoglycemic event threshold (i.e., the reading is below a threshold value). In some implementations, a hypoglycemic event is considered to be one or more hypoglycemic readings that occur within the same two hour time window (e.g., three hypoglycemic readings can be part of one hypoglycemic event). A hypoglycemic reading is a single blood glucose reading that is below a predefined hypoglycemic threshold. In some implementations, the predefined hypoglycemic threshold is a fixed value, e.g., 70 mg/dL. In some implementations, a user or physician may set the value differently.

In some implementations, client-side modules 106 can detect one or more hypoglycemic events since the last synchronization. Further, as shown in FIG. 5A, the client-side modules 106 can generate a prompt or alert 502 requesting a patient 122 to fill out a hypo survey (i.e., a hypoglycemic survey for an individual hypoglycemic event) related to the specific hypo event. On the other hand, if the client-side modules 106 do not detect any readings that meet the hypoglycemic event threshold, the client-side modules 106 can display a confirmation message on a user interface, as shown in FIG. 5B. The congratulatory text in FIG. 5B provides positive reinforcement to the patient 122 if no hypoglycemic events exists within two weeks of the current date. A View All button 503 can cause additional hypoglycemic events (e.g., older than two weeks) to be displayed.

In some implementations, the user interfaces as shown in FIGS. 5A and 5B can be displayed in response to a synchronization event. For example, when a synchronization event occurs, a prompt such as 502 illustrated in FIG. 5A is displayed shortly (e.g., within 5 seconds) if new readings contain one or more hypoglycemic event that occurred within two weeks from the current time (time of the synchronization event). In some implementations, a set of acceptance criteria can be set and used for triggering the display of prompt 502. For example, when synchronizing a meter that contains one or more readings below 70 mg/dL in the last two weeks, the prompt 502 can be displayed. On the other hand, when all of the readings are above 70 mg/dL (or the specified threshold), the prompt 502 is not displayed and the client device 102 may instruct the meter to synchronize at a subsequent time. The message "1 Hypo Event Detected" is modified according to the actual number of identified hypo events based on the data received.

In some implementations, the client-side modules 106 specify the timing of blood glucose readings and prompt the patient 122 with different user interfaces to facilitate hypoglycemic event data entry. In some implementations, when a hypoglycemic event is more than two weeks old, the patient 122 is not prompted to complete the survey. In some implementations, hypoglycemic events that are older than two weeks are shown differently in the user interface than the hypoglycemic events in the last two weeks. When the patient 122 has more than one hypo event in the last two weeks, the patient is prompted to provide hypo survey feedback for each of them. In some implementations, the hypo events are displayed in reverse chronological order. In some implementations, the hypo events are displayed in order based on the severity of the hypoglycemic event, from lowest blood glucose level to highest. In some implementations, the patient 122 can dismiss an alert by selecting "remind me later" or "I don't care" 501 as shown in FIG. 5A. In some implementations, at the end of a day, the client-side modules 106 generate a reminder to remind the user to complete any hypoglycemic event surveys that are incomplete.

Referring back to FIG. 4, in addition to identifying hypoglycemic events, the client-side modules 106 provide (406) a hypo events listing including one or more identified hypoglycemic events. For example, FIG. 5C illustrates a list 505 of hypoglycemic events. If a survey is not filled out by the patient 122 when prompted as shown in FIG. 5A, only the blood glucose (BG) value for that event is displayed. In addition to the BG value, an indication (such as Start Survey 504 and/or a blood draw symbol 506) is displayed to indicate that a report has not been filled out for a particular hypoglycemic event. On the other hand, if a survey has been filled out when prompted as shown in FIG. 5A, a symbol 508 is displayed. The displayed symbol 508 indicates that the user has entered survey data. Survey entry indicators 510 are displayed as shown in FIG. 5C.

In some implementations, for multiple readings in a short time period (e.g., an hour) the client-side modules 106 cluster the readings and prompt the user for a hypo survey on the first reading in each cluster. In general, the patient 122 need not report data for the other readings in each cluster. When the patient 122 does not enter data for the other readings, the survey can be applicable to each of readings in the cluster in accordance with some implementations. In some instances, the survey data is entered and reviewed by the person whose blood glucose is being monitored. In other instances, another user (such as a care giver or relative) enters the data, or a portion of the data.

In some implementations, the hypoglycemic events listed in FIG. 5C are sorted and displayed in reverse chronological order (most recent to least recent within the last two weeks). Though not shown in 5C, a "load more" button can be displayed. When clicked, more historical hypoglycemic events are displayed in the same reverse chronological order. In FIG. 5C, the date and time of each hypoglycemic event is displayed along with the BG value. If the hypoglycemic event is made up of multiple readings, the date and time and value of the occurrence of the first hypo reading in the event is displayed, with an icon that depicts the number of hypo readings in the hypo event.

In some implementations, if a survey has been completed for a single hypoglycemic event, three icons 510 are displayed across the cell in the user interface. The three icons 510 represent symptoms, treatment, and causes. In some implementations, the number of displayed icons is limited by available space in the user interface (e.g., showing only one icon for each of the categories). Selecting the icons 510 or other icons associated with the completed hypoglycemic event entry, a summary of the hypoglycemic event is displayed. An exemplary summary user interface is shown in FIG. 5J.

In some implementations, if the screen size is small, one icon is used to indicate a survey has been filled out. If a hypo survey has been partially completed, a different indicator is displayed in the row corresponds to the hypoglycemic event entry in the user interface. Selecting the indicator, the next screen to be completed in the hypo survey is displayed. In some implementations, if the hypoglycemic event is made up of multiple hypoglycemic readings, a window is displayed that shows each reading in the event. In some implementations, this window includes a Start button. Tapping or clicking the Start button begins the hypo survey.

Referring back to FIG. 4, once the client-side modules 106 receives instructions from the patient 122 to start the survey entries, the client-side modules 106 provide (408) the hypo survey associated with the hypoglycemic event. The client-side modules 106 further obtain (410) user feedback from the hypo survey and determine (412) whether a severe hypoglycemic event has occurred. The feedback includes (410) symptoms, causes, and/or treatment. The user feedback can be stored in the client database 238 on the client devices 102. In some implementations, the client database 238 includes information such as:

What symptoms did the patient feel?
What caused the patient to feel hypo (perceived cause)?
How did the patient treat the hypoglycemic event (treatment)?
Did the patient require assistance (severe hypo)?

The information listed above (symptoms, causes and treatments) can be stored separately (e.g., in separate tables in the client database 238) in some implementations. When requested, the client-side modules 106 retrieve the data stored in the client database 238, combine the data, and provide (414) one or more hypo reports that include at least a subset of the information listed above for display on the client devices 102. The hypo report includes at least a subset of user feedback from the hypo survey. An exemplary hypo report is shown in FIG. 5C in response to the patient's 122 selection of View Hypos, as shown in FIG. 5A. In addition to the hypo report, the client-side modules 106 provide (416) a summary comprising hypoglycemic event data entries, such as symptoms, causes, and treatments provided by the hypo survey, as illustrated in FIG. 5J.

FIGS. 5D-5J illustrate user interfaces for an exemplary survey and a summary of the exemplary survey. For example, as shown in FIG. 5D, a reading display 512 of 46 mg/dL indicates a hypoglycemic event has occurred at 3:21 PM on Apr. 18, 2012. In some implementations, the first section of the hypo survey is to enter the symptoms. In some implementations, to facilitate the entries (e.g., if this is the patient's 122 first time filling out a hypo survey), the patient 122 is shown a pop-up that includes a definition for each symptom. The patient 122 can close the pop-up and begin filling out the hypo survey.

Once the patient 122 begins filling out the hypo survey, the client-side modules 106 receive the patient 122 selection of one or more symptoms that apply for that hypoglycemia event 512 and display the selection. In some implementations, the list of symptoms is arranged from most to least common and includes a predetermined number of symptoms (e.g., approximately 20). In some implementations, the order of symptoms can be customized and machine-learned so that the symptoms most common to the individual patient 122 are displayed at the beginning of the list. In some implementations, icons 514 can turn different color and/or shade etc. when selected. Deselecting the icons 514 can restore the color and/or shade. An exemplary list of symptoms that can be displayed as icons includes trembling 514-1, nervous 514-2, heart pounding, sweating, fatigue, unusual hunger, discomfort in legs, feeling cold, numb lips, depressed, hard to focus, light headed, blurred vision, headache, queasy stomach, slurred speech, difficulty walking, difficulty driving, no symptoms, and other.

Turning to FIG. 5E, in some implementations, an instructive tool tip 515 regarding symptoms can be displayed to help the patient 122 determine the type of information entered in the symptoms user interface. In some implementations, if a patient 122 does not see his/her symptom listed, the patient 122 can create a custom symptom. For example, in some implementations, the client-side modules 106 display a section labeled "Anything else you want to add." In response to selecting this section, the client-side modules 106 display a text box for the patient 122 to enter the symptom(s). Upon completion, the client-modules 106 receive an indication from the patient 122 (e.g., the patient 122 clicks a Done button) and close the text box.

Referring back to FIG. 5D, once the symptoms are selected, the patient 122 can tap or click a Next button 518 to save the symptom(s) and move on to the next section, causes. In some instances, the patient 122 may not get to the end (e.g., may not click the Quit button 516). Since each incremental set of data is important, clicking the Next button 518 saves the incremental set of data to the client database 238.

In some implementations, the second section of the hypo survey is to enter the causes. For example, as shown in FIG. 5F, the client-side modules 106 display a user interface for the patient 122 to enter the causes for the hypoglycemic event that occurred at 3:21 PM on Apr. 18, 2012. In some implementations, to facilitate the entries (e.g., if this is the patient's 122 first time filling out the hypo survey), the client-side modules 106 display a pop-up to the patient 122 that includes the definition of each cause. The patient 122 can close the pop-up and continue filling out the hypo survey. An exemplary list of causes that are displayed as icons includes: excess insulin, excess medication, unplanned activity, exercise, delayed meal, incorrect carb calc (carbohydrate calculation by the patient), schedule change, alcohol, don't know, and other.

In some implementations, the client-side modules 106 receive the patient 122 selection of one or more causes that apply for that hypoglycemia event 512 and display the selection. In some implementations, an icon 524 can turn different color and/or shape etc. when selected. Turning to FIG. 5G, in some implementations, an instructive tool tip 529 regarding causes can be displayed to help the patient 122 determine the type of information entered in the causes user interface. Referring back to FIG. 5F, in some implementations, the client-side modules 106 display the instructive tool tip in response to the patient 112 selection of a tool tip icon 520.

In some implementations, if a patient 122 does not see his/her cause listed, the patient 122 can create a custom cause. For example, in some implementations, the client-side modules 106 display a section labeled "Other" 522. In response to selecting the other section 522, the client-side modules 106 display a text box for the patient 122 to enter the cause(s). Upon completion, the client-modules 106 receive an indication from the patient 122 (e.g., the patient 122 clicks a Done button) and close the text box.

Once the causes are selected, the patient 122 can click the Next button 528 to save the cause(s) and move on to the next section (treatments). If the patient 122 wants to edit the symptoms entered previously, the patient 122 can click the Back button 526 to return to the symptoms screen.

In some implementations, the third section of the hypo survey is to enter the treatments. For example, as shown in FIG. 5H, the client-side modules 106 display a user interface for the patient 122 to enter the treatments for the hypoglycemic event that occurred at 3:21 PM on Apr. 18, 2012. In some implementations, to facilitate the entries (e.g., if this is the patient's 122 first time filling out the hypo survey), the client-side modules 106 display a pop-up to the patient 122 that includes the definition of each treatment. The patient 122 can close the pop-up and continue filling out the hypo survey.

In some implementations, the client-side modules 106 receive the patient 122 selection of one or more treatments that apply for that hypoglycemia event 512 and display the selection. In some implementations, an icon 534 can turn different color and/or shape etc. when selected. An exemplary list of treatments that can be displayed as icons includes: juice, food, glucose tablet, glucose gel, and other. If the person required assistance to treat the hypo event, an exemplary list of treatments for severe hypoglycemic events includes: glucagon injection, EMT assistance, and Emergency Room.

For each treatment selected, the client-side modules 106 can display a pop-up window for the patient 122 to provide more details. For example, the quantity of the treatment such as 15 g of sugar vs. 30 g of sugar and/or clinical implication of whether the patient 122 is over treating in the hypoglycemic event can be added as treatment details. As shown in FIG. 5H, in response to the patient's 122 selection of the glucose tablet icon 534, the client-side modules 106 display a pop-up window 532. In the pop-up window 532, the number of glucose tablets can be entered. Once the patient 122 fills out more details of the treatment in the pop-up window 532, the patient 122 can click Save to return to the treatment page illustrated in FIG. 5H.

Turning to FIG. 5I, in some implementations, an instructive tool tip 535 regarding treatments is displayed to help the patient 122 determine the type of information to enter in the treatments user interface. Referring back to FIG. 5H, in some implementations, the client-side modules 106 display the instructive tool tip 535 in response to patient selection of a tool tip icon 537.

In some implementations, if a patient 122 does not see his/her treatment listed, the patient 122 can create a custom cause. For example, in some implementations, the client-side modules 106 display a section labeled "Other" 534. In response to selecting the section 534, the client-side modules 106 display a text box for the patient 122 to enter the treatment(s). Upon completion, the client-modules 106 receive an indication from the patient 122 (e.g., the patient 122 clicks a Done button) and close the text box.

In some implementations, the client-side modules 106 also display an on/off switch 536 to allow the patient 122 specify if the patient 122 required medical assistance for the particular hypoglycemic event. In some implementations, the client-side modules set and display No as default to indicate the patient 122 did not require medical assistance. The patient 122 can toggle the on/off switch 536 to indicate that the patient 122 did require assistance. A hypoglycemic event that needed assistance is a severe hypoglycemic event. In response to receiving the yes selection the switch 536, the client-side module 106 can further provide an entry field to allow the patient 122 specific the type of assistance provided. In some implementations, the user entering the type of assistance provided may be different from the patient 122, for whom the readings were taken. Once the treatments are selected, the patient 122 can click the Next button 538 to save the treatment(s) and see a summary of the hypo survey. If the patient 122 wants to edit the symptoms and causes entered previously, the patient 122 can click the Back button 539 to return to the symptoms and/or causes screen.

In some implementations, the final section of the hypo survey is a summary. The client-side module 106 retrieves the symptoms, causes, and treatments stored in the client database 238 and displays the survey as shown in FIG. 5J. To edit a specific section of the hypo survey, the patient 122 can click edit icons 540. In response to receiving the edit selection input, the client-modules 106 displays the corresponding section of the hypo survey for editing. When the patient 122 is satisfied with the survey entries, the patient 122 can click the Save button 548.

As described above with respect to FIGS. 5D-5J, the survey can include the following sections:
 What symptoms did you feel (FIGS. 5D-5E)?
 What caused you to feel hypoglycemic (e.g., perceived causes, FIGS. 5F-5G)?
 How did you treat your hypoglycemic event (e.g., treatments, did you require assistance, FIGS. 5H-5I)?

The client-modules 106 obtain user feedback from the hypo survey and store the data in the client database 238. In some implementations, each of the sections in the hypo survey is displayed in a separate user interface, e.g. symptoms (FIG. 5D), causes (FIG. 5F), and treatments (FIG. 5H). For each of the above sections, the patient 122 can choose from stock answers (e.g., the symptoms icons 514 in FIG. 5D, the cause icon 524 in FIG. 5F, and the treatment icon 534 in FIG. 5H) as well as enter free form text. In some implementations, since the hypoglycemic event data can be stored in the client database 238, the user interfaces as shown in FIG. 5A-5J can be displayed without the client device 102 being connected to the communications network 104. In some implementations, the user interfaces as shown in FIG. 5A-5J can be displayed after other synchronization prompts, e.g., sync successful.

It should be understood that the particular order in which the operations in FIG. 4 have been described is merely exemplary and is not intended to indicate that the described order is the only order in which the operations could be performed. One of ordinary skill in the art would recognize various ways to reorder the operations described herein. For brevity, these details are not repeated here.

The foregoing description of the user interfaces with respect to FIGS. 5D-5J, for purpose of explanation, has been described with reference to specific embodiments. However, the illustrative discussions above are not intended to be exhaustive or to limit the invention to the precise forms disclosed. Many modifications and variations are possible in view of the above teachings. For example, in some implementations, the client-side modules 106 can display a None field within each question (e.g., no symptoms, no treatment, don't know cause etc.) In another implementation, a patient 122 can fill out a hypo survey independent of a reading value. The client-side modules 106 can display a Quick Add screen or allow the patient 122 to choose "Feeling Hypo" for easier access. In addition, the client-side modules 106 can provide search functions so that the patients 122 can easily find the hypoglycemic events that they have not responded to in the history list or reports list. In yet another example, the questions in the survey as shown in FIGS. 5A-5I can be customizable and configured. The illustrated implementations were chosen and described in order to best explain the principles of the invention and its practical applications, to thereby enable others skilled in the art to best use the invention and various described embodiments with various modifications as are suited to the particular use contemplated.

In some implementations, the client-side modules 106 transmit the hypoglycemia data to a server 108. The data can be uploaded to the server 108 automatically or upon request in accordance with some implementations. In addition to upload, the server 108 can receive the data via other methods, such as by email, fax, scan of print, and/or manual entries, among others. Utilizing (418) the hypoglycemic event information, such as the information one or more hypo reports and a plurality of blood glucose readings, the server 108 produces one or more glucose data reports. The generated reports can then be provided (420) to healthcare providers (e.g., doctors and nurses) and/or payers (e.g., insurance companies). FIGS. 5K-5M illustrate examples of glucose data reports.

FIG. 5K illustrates a hypo awareness grid 550 that can be displayed on a client device 102 or on a device 130. In some implementations, the server 108 receives a request from the client-side modules 106 or the device 130 to access the hypoglycemic awareness grid. In some implementations, the access uses a web application hosted by the server 108. Upon receiving the request, the server 108 retrieves the data from the hypoglycemic database 110, and transmits the results to the requestor for display on the client device 102 or the device 130. In some implementations, the results include analysis of the hypo event data, including identified patterns.

For example, in FIG. 5K, the top of the page displays a date picker 552 that allows the user to select the date interval in which to display historical hypoglycemic events. The default time frame 554 is 30 days in some implementations. Below the data picker 552, a legend 556 representing the number of symptom and BG level combination occurrences is displayed. One occurrence may be in a lighter color and/or shade than six plus occurrences in some implementations. Next to the legend 556, the number of hypo surveys filled out relative to the number of hypoglycemic events within the selected date interval 552 is displayed. In FIG. 5K, there were eight hypoglycemic events detected by the client device 102. Among the eight events, six of them have hypo surveys filled out.

The hypo awareness view displays a grid of hypoglycemic events that correspond to symptoms reported by the user 122. The static y-axis corresponds to BG values. Increments (e.g., of two) are displayed, from top to bottom, e.g., starting at 70 mg/dL and ending at 30 mg/dL. In FIG. 5K, the last entry listed is "<30 mg/dL". The x-axis displays a list of individual symptoms that are categorized from autonomic to cognitive. Every stock symptom that was selected by the user during the survey is displayed in the x-axis. The last entry listed in symptoms is "No Symptoms". In some implementations, the symptoms listed on x-axis are sorted and displayed from mild to severe.

In some implementations, the hypo grid is divided into quadrants. For example, in FIG. 5K, quadrants 560 are be defined by: 70-50, autonomic symptoms; 50-30 autonomic symptoms; 70-50, cognitive symptoms; and 50-30 cognitive symptoms. Examples of autonomic symptoms of hypoglycemic events are trembling, nervous, heart pounding, sweating, and unusual hunger. Cognitive symptoms are due to a shortage of glucose in the brain that affects the function of neurons. Examples of cognitive symptoms are fatigue, discomfort in legs, feeling cold, numb lips, depressed, hard to focus, light-headed, blurred vision, headache, queasy stomach, slurred speech, difficulty walking, and difficulty driving.

In FIG. 5K, if a survey as shown in FIGS. 5A-5J has been filled out for a hypoglycemic event, an indicator (e.g., a square 558) is recorded in one or more cells that correspond to the BG values and appropriate symptoms. If the same (BG level, symptom) pair occurred for multiple hypo events, some implementations shade the square 558 according to the legend 556, with the number of occurrences listed in the square. The color or shading of the square 558 corresponds to the legend 556. The hypo awareness report as shown in FIG. 5K directly maps low glucose readings with associated individual-specific symptoms. This data visualization allows providers, such as clinicians, at a glance, to determine if patients have hypoglycemia unawareness. This data visualization also helps to raise patients' hypoglycemia awareness.

In some implementations, in response to detecting a hovering event over a square, a tooltip is displayed corresponding to the symptom. In some implementations, a black box with a symptom description is displayed around the square when hovering. Also not shown in FIG. 5K, in some implementations, a composite score based on frequency, severity, and degree of unawareness of the hypoglycemia can be calculated and displayed.

FIG. 5L illustrates a hypo patterns grid 565 that can be displayed on a client device 102 or a device 130. Similar to the hypo awareness grid 550 in FIG. 5K, the top of the page displays a date picker 566 that allows the user to select the timeframe in which to display historical hypoglycemic events. Though not shown in FIG. 5L, in some implementations, the user can select the month to view by tapping left or right arrows next to the month listed. The first time the page is loaded, in some implementations, the current month is displayed. In some implementations, the days that do not fall in the selected timeframe can be grayed out. In some implementations, the occurrence of hypoglycemic events can still be graphically depicted in the hypoglycemic patterns grids 565 in the days before and after the selected month(s). In addition to the data picker 566, also similar to hypo awareness grid 550 in FIG. 5K, the number of hypo surveys filled out relative to the number of hypoglycemic events happened within the selected date interval is displayed.

In the hypo patterns grid 565, a legend 568 representing time periods in a day. Each time period can be displayed in a different color and/or shade etc. For example, in FIG. 5L, each day is divided to four time periods: 12 AM-6 AM, 6 AM-12 PM, 12 PM-6 PM, 6 PM-12 AM. The time period 12 AM to 6 AM is in a different color and/or shade from other time periods.

The hypo patterns grid 565 displays a pattern of hypoglycemic events occurrences during different time periods in a day. Each row in the calendar view represents a full week. If a hypoglycemic event occurred during one of the time periods, the portion of the day block that corresponds to the time periods is colored and/or shaded. If multiple hypoglycemic events occurred on the same day in the same time period, the coloring and/or shading can be the same as if one hypoglycemic event occurred in that timeslot on that day. The indicators 570 are colored and/or shaded according to the legend 568.

In some implementations, the hypo patterns report 565 maps hypoglycemic events by time of day and day of the week. It helps differentiate between random hypoglycemia and more predictable hypoglycemic events that are linked to daily and weekly life routines and habits. For example, the indicators 570-1 and 570-4 are the same color and/or shade in FIG. 5L, representing at least one hypoglycemic event happened on Saturday Aug. 2, 2014 between 6 PM and 12 AM and at least one hypoglycemic event happened on Saturday Aug. 9, 2014 between 6 PM and 12 AM. Similarly, the indicators 570-2 and 570-6 are the same color and/or shade in FIG. 5L, representing at least one hypoglycemic event happened on Wednesday Aug. 6, 2014 between 6 PM and 12 AM and at least one hypoglycemic event happened on Wednesday Aug. 13, 2014 between 6 PM and 12 AM. A pattern may be drawn to establish linkages between predictable weekend and/or Wednesday afternoon hypoglycemic events and the weekly life routines and habits. On the other hand, indicators 570-3, 570-5, and 570-7 are of different colors and/or shades and displayed in different date blocks. These indicators may help differentiate random hypoglycemic events from the more predictable hypoglycemic events marked by indicators 570-1, 570-4, 570-2, and 570-6.

FIG. 5M illustrates a hypo day report 575 that can be displayed on a client device 102 or a device 130. The hypo day report 575 displays contextual information from each hypoglycemic event, plus the corresponding data for 12 hours before and after the episode in some implementations. This report provides detailed information around each hypoglycemic event, thereby enhancing clinical decision-making. It also turns events into teachable moments, improving patients' insight into how to prevent and treat hypoglycemia. Similar to the hypo awareness grid 550 in FIG. 5K and the hypo patterns 565 in FIG. 5L, the top of the page displays a date picker 576 that allows the user to select the timeframe in which to display historical hypoglycemic events. Also similar to hypo awareness grid 550 in FIG. 5K, the default time frame is 30 days in some implementations.

The list of hypoglycemic events in the hypo day report 575 can be sorted and displayed in different orders. In some implementations, the hypoglycemic events can be shorted by BG values. In response to a selection of BG List button 578, the hypo survey results can be ordered from lowest to highest glucose reading. In response to a selection of Time of Day button 580, the hypo survey results can be ordered from morning to evening, bucketed into different periods of the day. In some implementations, the ordering by time of day is set as the default.

Below the BG List 578 and Time of Day 580, the hypoglycemic events detected within the selected timeframe are displayed. For each hypoglycemic event, the BG value, time of the event, and user feedback from the survey are displayed. In some implementations, severe hypo events which required assistance are called out and flagged in the hypoglycemic day report 575. In some implementations, if the user has not filled out a survey, a message is displayed across the user feedback columns to remind the user to fill out the survey. Clicking on the message can take the user to the survey user interfaces as shown in FIGS. 5A-5J.

In some implementations, above each day where at least one hypoglycemic event has been detected, an indicator 588 representing the time period in a day of the hypoglycemic event is displayed. In some implementations, the color and/or shading of the indicator 588 is consistent with the legend 568 displayed in the hypo patterns grid 565, as shown in FIG. 5L. In addition to using different colors and/or shadings representing different time periods in a day of the hypoglycemic event, in some implementations, the BG value 587 can displayed using the color and/or shading consistent with the legend 556 in the hypo awareness grid 550, as shown in FIG. 5K. For example, if multiple symptoms occurred for the same range of BG values, the BG value 587 can be colored and/or shaded according to the legend 556.

For each hypoglycemic event, a graph icon 582 is displayed. By clicking on the graph icon 582, a time of day graph 584 appears. While the time of day graph 584 is displayed, clicking on the graph icon 582 can hide the time of day graph 584. The time of day graph 584 is a 24 hour graph that has hypo hour in the middle of the line in accordance with some implementations. The graph 584 has an x-axis that spans 24 hours. The x-axis starts 12 hours before the time of the hypoglycemic event (e.g., the timestamp of first reading for the hypoglycemic event). The y-axis auto-adjusts to fit the data present in the 24-hour interval. The user can set a lower limit BG value after meal and an upper limit BG value before meal. Both limits are shaded on the graph 584. The line represents the before meal upper limit set by the user. The tick marks on the x-axis display every 2 hours on the hour. Below each end of the x-axis the day of week and date is displayed. Each BG value reading is represented by an individual data point. The BG values 586 are colored based on whether they fall below, within or above the user's set target ranges. Readings tagged as before meal are considered to be within range if they fall within the lower limit and upper limit. In some implementations, though not shown in FIG. 5M, a line is used to connect the BG values 586.

In some implementations, the reports described above with respect to FIGS. 5K-5M can be requested by patients, healthcare providers, or payers. In some implementations, an access control module 338 on the server 108 can authenticate and authorize the request before retrieve the data from the hypoglycemic database 110, generate reports based on the data, and transmitting the reports. For example, a patient 122 may want to access reports generated based on his blood glucose readings uploaded to the server 108. The client-side modules 106 on a client device 102 used by the patient 122 obtains the patient's 122 identifier and sends the credentials to the server 108 for authentication and authorization. The access control module 338 compares the received credentials with the information stored in the user database 342 for authentication and authorization. Upon successful authentication and authorization, the server 108 transmits the requested reports generated based on the patients' 122 uploaded readings to the client device 102 for display. In another example, the patient 122 may upload some of his readings to share with a doctor 132. The modules on the device 130 used by the doctor 130 receive the doctor's 132 identifier and sends the credentials to the server 108 for authentication and authorization. Upon successful authentication and authorization, the server 108 transmits the requested reports generated based on the patients' 122 shared readings to the device 130 for display. In yet another example, a payer (e.g., an insurance company) may want to disable the reports for a specific provider 132 that is not part of the payer's network. When the specific provider 132 attempts to access the reports, without successful authentication and authorization, the server 108 does not transmit the requested reports generated based on the patients' 122 uploaded readings to the device 130 for display.

FIGS. 6A-6F provide a flow diagram of a method 600 for receiving hypoglycemic event data, analyzing the data, and providing reports based on the data in accordance with some implementations. Various operations of the method 600 are performed (602) at a computing device, such as the server system 108 shown in FIG. 3 and/or the client device 102 shown in FIG. 2 and/or the device 130, having one or more processors (e.g., the CPU 202 in client device 102 and/or the CPU 302 in server 108), a display device (e.g., the display 206 as part of the client device 102 and/or a display as part of the device 130), and memory (e.g., the memory 212 in client device 102 and/or the memory in server 108) storing one or more programs configured for execution by the one or more processors.

The computing device first receives (604) a plurality of blood glucose readings for a person (e.g., the patient 122). Each reading includes: a blood glucose value and a timestamp (e.g., date and time) that indicates when the respective reading was taken. In some implementations, the person (e.g., the patient 122 or an assistant) is prompted (606) to provide information only for hypoglycemic events that are less than two weeks old. In some implementations, a plurality of blood glucose readings that are below the predefined hypoglycemic event threshold comprise (608) a single hypoglycemic event when the timestamps of the blood glucose readings are within a two hour time period.

Upon receiving the readings, the computing device compares (610) each blood glucose reading of the plurality to a predefined hypoglycemic event threshold and identifies a hypoglycemic event when a respective blood glucose reading is below the predefined hypoglycemic event threshold. In some implementations, the predefined hypoglycemic threshold is (612) defined as a fixed value (e.g., 70 mg/dL), is set by the person (e.g., the patient 122), or is set by a doctor. In some implementations, each blood glucose reading that is below the predefined hypoglycemic event threshold is (614) identified as a distinct hypoglycemic event.

Having identified the hypoglycemic event, the computing device prompts (616) the person (e.g., the patient 122 or an assistant) to provide information associated with each hypoglycemic event for at least a subset of the identified hypoglycemic events. In some implementations, the information requested includes one or more of: symptoms associated with the respective hypoglycemic event; perceived causes of the respective hypoglycemic event; and treatment for the respective hypoglycemic event. In response to the prompting, the computing device obtains (630) feedback from the person (e.g., the patient 122) about the identified hypoglycemic events uses a graphical user interface on the display device. In some implementations, the obtained feedback includes (632): feedback regarding symptoms; feedback regarding causes; and feedback regarding treatment.

For example, as shown in FIG. 5D, the computing device displays (618) a plurality of hypoglycemic event symptom icons and records (620) user selection of one or more of the plurality of hypoglycemic event symptom icons (e.g., the icons 514-1 and 514-2). In FIG. 5D, the obtained feedback includes symptoms such as trembling as represented by icon 514-1 and nervous as represented by icon 514-2. In another example, as shown in FIG. 5F, the computing device displays (622) a plurality of hypoglycemic event cause icons and records (624) user selection of one or more of the plurality of hypoglycemic event cause icons (e.g., the icon 524). In FIG. 5F, the obtained feedback include a cause of excess medication as represented by icon 524. In yet another example, as shown in FIG. 5H, the computing device displays (626) a plurality of hypoglycemic event treatment icons and records (628) user selection of one or more of the plurality of hypoglycemic event treatment icons (e.g., the icon 534). In FIG. 5H, the obtained feedback includes a treatment of glucose tablet as represented by icon 534-1.

In some implementations, the feedback gathered is stored in the client device 102 (e.g., the client database 238) and/or the server 108 (e.g., the hypoglycemic event database 110). In response to requests from the client device 102 and/or the device 130, the client device 102 and/or the server 108 provide (634) a report on the display device (e.g., on the display 206 as part of the client device 102 or a display as part of the device 130) that includes at least a subset of the obtained feedback. In some implementations, the provided report includes (636) a hypo awareness grid (FIG. 5K). One axis of the hypo awareness grid shows blood glucose level and a second axis of the grid shows reported symptoms. Each entry in the grid indicates how many hypoglycemic events had a specific (glucose level, symptom) pair. In some implementations, the provided report includes (638) a graphical presentation of information regarding blood glucose levels before and after one or more hypoglycemic events (e.g., FIG. 5L and FIG. 5M). In accordance with some implementations, the provided report includes (640) one or more recommended changes to activities of the person.

In some implementations, the glucose data report module 234 on the client device 102 and/or the glucose data report module 334 further analyze (642) the hypoglycemic events and the obtained feedback to identify one or more patterns of hypoglycemic events and include (648) the identified patterns of hypoglycemic events in the provided report (e.g., FIGS. 5K-5M). In some implementations, the identified patterns include (644) a correlation between hypoglycemic events and time of day or day or week (e.g., FIG. 5L and FIG. 5M). In some other implementations, the identified patterns indicate (646) that the person is unaware when low blood glucose levels are occurring (e.g., FIG. 5K).

In some implementations, based on the feedback and the readings, the client device 102 and/or the server 108 determine (650) that a severe hypoglycemic event occurred when the person indicates that assistance was required. The assistance information can be gathered by the client device 102 as shown in FIG. 5H. The severe hypoglycemic event can be indicated in the patterns displayed and reports generated.

The various hypoglycemic event analysis operations of the method 600 described above can be performed on the server system 108 shown in FIG. 3 and/or the client device 102 shown in FIG. 2. As explained above with respect to FIG. 2 and FIG. 3, the functionality described in FIGS. 2 and 3 may be implemented either on the client device 102, on the server 108, or both. Various implementations allocate functionality between the client device 102 and the server 108 in various ways. In some implementations, the allocation of functionality is configurable based on individual devices. For example, in some implementations, the client device 102 receives blood glucose readings from the meter 120 and obtains feedback from the patient 122. The client device then transmits (652) the received blood glucose readings and obtained feedback to a second device (e.g., the server 108) to identify one or more patterns of hypoglycemic events. The identified patterns can then be accessed by doctors and/or nurses and/or insurance companies.

Figure 7A:
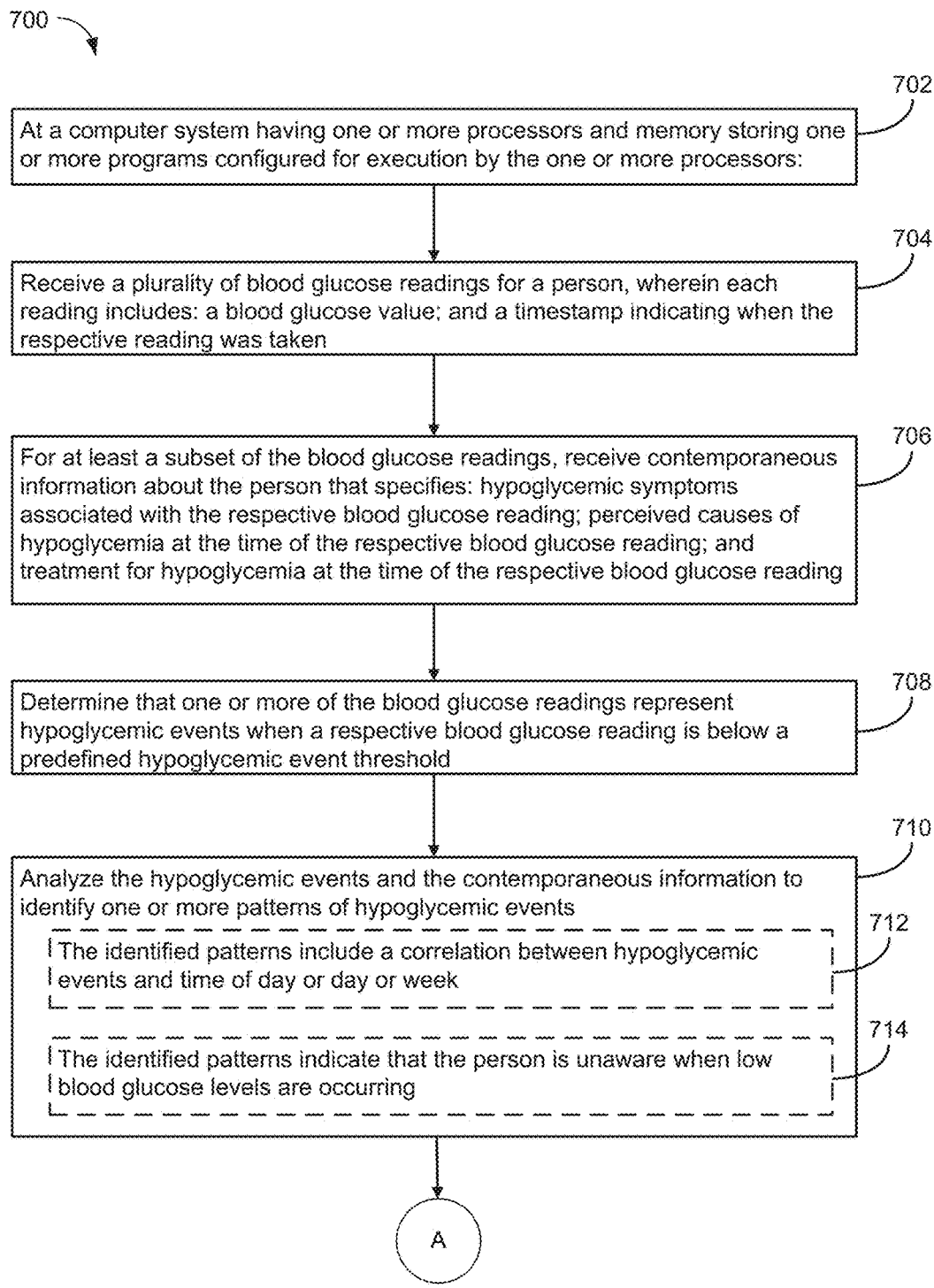
FIGS. 7A-7B illustrate a flowchart representing a method for managing low blood glucose levels, in accordance with some implementations.
Figure 7B:
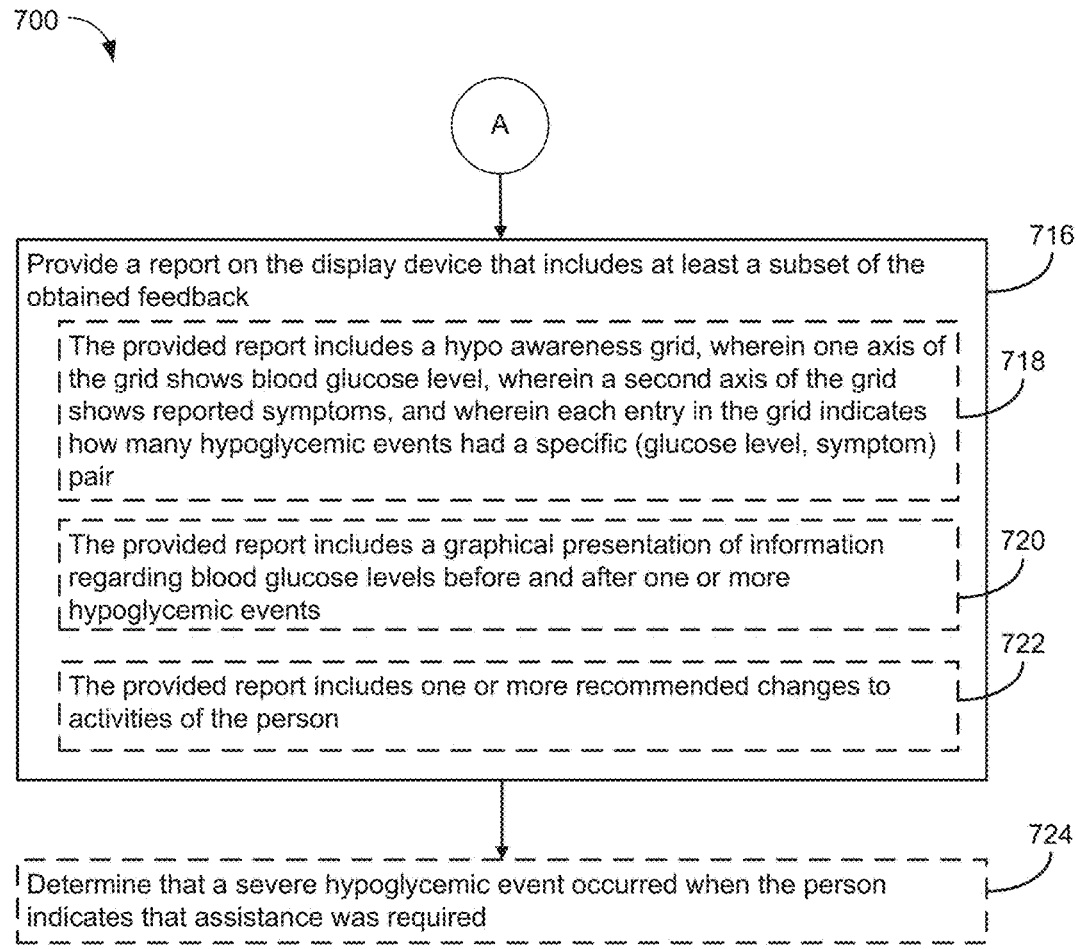

FIGS. 7A-7B illustrate a flow diagram of a method 700 for managing low blood glucose levels, in accordance with some implementations. Various operations of the method 700 are performed (702) at a computing device, such as a server system 108 as shown in FIG. 3 and/or a client device 102 shown in FIG. 2 and/or a device 130. The computing device has one or more processors (e.g., the CPU 202 in client device 102 and/or the CPU 302 in server 108) and memory (e.g., the memory 212 in client device 102 and/or the memory in server 108) storing one or more programs configured for execution by the one or more processors.

The computing device first receives (704) a plurality of blood glucose readings for a person (e.g., the patient 122). The computing device then for at least a subset of the blood glucose readings, receives (706) contemporaneous information about the person that specifies: hypoglycemic symptoms associated with the respective blood glucose reading, perceived causes of hypoglycemia at the time of the respective blood glucose reading, and treatment for hypoglycemia at the time of the respective blood glucose reading. Based on the information, the computing device then determines (708) that one or more of the blood glucose readings represent hypoglycemic events when a respective blood glucose reading is below a predefined hypoglycemic event threshold. The computing device also analyzes (710) the hypoglycemic events and the contemporaneous information to identify one or more patterns of hypoglycemic events and provides (716) a report that includes the identified patterns of hypoglycemic events and at least a subset of the contemporaneous information.

For example, as described above with respect to FIG. 1, the readings are obtained from the meter 120 by the client device 102 after blood samples were supplied to the meter 120. In some implementations, the readings are subsequently uploaded to the server 108 from the client device 102 via the communication network 104. In some implementations, each reading includes a blood glucose value and a timestamp (e.g., date and time) that indicates when the respective reading was taken. Based on the readings, the computing device determines if one or more hypoglycemic events has occurred and prompts the user to fill out the survey as shown in FIGS. 5A-5J in near real time. The computing device also analyzes the hypoglycemic events, identifies patterns and provides reports as shown in FIGS. 5K-5M.

In some implementations, the provided report includes (718) a hypo awareness grid (FIG. 5K). One axis of the hypo awareness grid shows blood glucose level and a second axis of the grid shows reported symptoms. Each entry in the grid indicates how many hypoglycemic events had a specific (glucose level, symptom) pair. In some implementations, the provided report includes (720) a graphical presentation of information regarding blood glucose levels before and after one or more hypoglycemic events (e.g., FIG. 5L and FIG. 5M). In accordance with some implementations, the provided report includes (722) one or more recommended changes to activities of the person. The recommended changes typically include one or more of: changes to exercise, changes to eating, and/or changes to taking medication.

In some implementations, the identified patterns include (712) a correlation between hypoglycemic events and time of day or day or week (e.g., FIG. 5L and FIG. 5M). In some other implementations, the identified patterns indicate (714) that the person is unaware when low blood glucose levels are occurring (e.g., FIG. 5K).

In some implementations, based on the feedback and the readings, the computing device determines (724) that a severe hypoglycemic event occurred when the person indicates that assistance was required. The assistance information can be gathered by the client device 102 as shown in FIG. 5H. The severe hypoglycemic event can be indicated in the patterns displayed and reports generated.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without changing the meaning of the description, so long as all occurrences of the first element are renamed consistently and all occurrences of the second element are renamed consistently. The first element and the second element are both elements, but they are not the same element.

As used in the description of the implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," as well as the terms "includes" and/or "including" when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to," depending on the context. Similarly, the phrase "if it is determined" or "if (a stated condition or event]) is detected" may be construed to mean "upon determining" or "in response to determining" or "upon detecting (the stated condition or event)" or "in response to detecting (the stated condition or event)," depending on the context.

The foregoing description, for purpose of explanation, has been described with reference to specific implementations. However, the illustrative discussions above are not intended to be exhaustive or to limit the invention to the precise forms disclosed. Many modifications and variations are possible in view of the above teachings. The implementations were chosen and described in order to best explain the principles of the invention and its practical applications, to thereby enable others skilled in the art to best utilize the invention and various implementations with various modifications as are suited to the particular use contemplated.

What is claimed is:

1. A method for understanding and managing low blood glucose levels, comprising:
at a computer system having one or more processors, a display device, and memory storing one or more programs configured for execution by the one or more processors:
receiving a plurality of blood glucose readings for a person, wherein each reading includes:
a blood glucose value; and
a timestamp indicating when the respective reading was taken;
comparing each blood glucose reading of the plurality to a predefined hypoglycemic event threshold, and identifying a hypoglycemic event when a respective blood glucose reading is below the predefined hypoglycemic event threshold;
for at least a subset of the identified hypoglycemic events, prompting the person to provide information associated with each hypoglycemic event using a graphical user interface on the display device, wherein the prompting includes displaying a plurality of hypoglycemic event icons, according to a stored sort order, corresponding to the information requested, and wherein the information requested includes one or more of:
    symptoms associated with the respective hypoglycemic event;
    perceived causes of the respective hypoglycemic event; and
    treatment for the respective hypoglycemic event;
in response to the prompting, obtaining feedback from the person about the identified hypoglycemic events using the graphical user interface on the display device;
updating the stored sort order for the plurality of hypoglycemic event icons based on the obtained feedback; and
providing a report on the display device that includes at least a subset of the obtained feedback.

2. The method of claim 1, wherein the obtained feedback includes:
    feedback regarding symptoms;
    feedback regarding causes; and
    feedback regarding treatment.

3. The method of claim 1, wherein the person is prompted to provide information only for hypoglycemic events that are less than two weeks old.

4. The method of claim 1, further comprising determining that a severe hypoglycemic event occurred when the person indicates that assistance was required.

5. The method of claim 1, wherein the predefined hypoglycemic threshold is defined as a fixed value, set by the person, or set by a doctor.

6. The method of claim 1, wherein each blood glucose reading that is below the predefined hypoglycemic event threshold is identified as a distinct hypoglycemic event.

7. The method of claim 1, wherein a plurality of blood glucose readings that are below the predefined hypoglycemic event threshold comprise a single hypoglycemic event when the timestamps of the blood glucose readings are within a two hour time period.

8. The method of claim 1, wherein the provided report includes a hypo awareness grid, wherein one axis of the grid shows blood glucose level, wherein a second axis of the grid shows reported symptoms, and wherein each entry in the grid indicates how many hypoglycemic events had a specific (glucose level, symptom) pair.

9. The method of claim 1, wherein the provided report includes a graphical presentation of information regarding blood glucose levels before and after one or more hypoglycemic events.

10. The method of claim 1, wherein obtaining feedback from the person about the identified hypoglycemic events comprises:
    recording user selection of one or more of the plurality of hypoglycemic event icons.

11. The method of claim 1, further comprising:
    transmitting the received blood glucose readings and obtained feedback to a second computing device to identify one or more patterns of hypoglycemic events.

12. The method of claim 11, wherein the identified patterns include a correlation between hypoglycemic events and time of day or day or week.

13. The method of claim 11, wherein the identified patterns indicate that the person is unaware when low blood glucose levels are occurring.

14. The method of claim 1, further comprising:
    analyzing the hypoglycemic events and the obtained feedback to identify one or more patterns of hypoglycemic events; and
    including the identified patterns of hypoglycemic events in the provided report.

15. The method of claim 1, wherein the provided report includes one or more recommended changes to activities of the person, and wherein the recommended changes are associated with exercising, eating, or taking medication.

16. The method of claim 1, wherein updating the stored sort order for the plurality of hypoglycemic event icons includes sorting the plurality of hypoglycemic event icons according to how commonly each hypoglycemic event icon is selected by the person.

17. A computer system comprising:
    one or more processors;
    a display device; and
    memory storing one or more programs configured for execution by the one or more processors including instructions for:
        receiving a plurality of blood glucose readings for a person, wherein each reading includes:
            a blood glucose value; and
            a timestamp indicating when the respective reading was taken;
        comparing each blood glucose reading of the plurality to a predefined hypoglycemic event threshold, and identifying a hypoglycemic event when a respective blood glucose reading is below the predefined hypoglycemic event threshold;
        for at least a subset of the identified hypoglycemic events, prompting the person to provide information associated with each hypoglycemic event using a graphical user interface on the display device, wherein the prompting includes displaying a plurality of hypoglycemic event icons, according to a stored sort order, corresponding to the information requested, and wherein the information requested includes one or more of:
            symptoms associated with the respective hypoglycemic event;
            perceived causes of the respective hypoglycemic event; and
            treatment for the respective hypoglycemic event;
        in response to the prompting, obtaining feedback using the graphical user interface on the display device;
        updating the stored sort order for the plurality of hypoglycemic event icons based on the obtained feedback; and
        providing a report on the display device that includes at least a subset of the obtained feedback.

18. The computer system of claim 17, wherein updating the stored sort order for the plurality of hypoglycemic event icons includes sorting the plurality of hypoglycemic event icons according to how commonly each hypoglycemic event icon is selected by the person.

19. The computer system of claim 17, further comprising:
    transmitting the received blood glucose readings and obtained feedback to a second computing device to identify one or more patterns of hypoglycemic events.

20. A non-transitory computer readable storage medium storing one or more programs configured for execution by a computing device having one or more processors and memory, the one or more programs comprising instructions for:

receiving a plurality of blood glucose readings for a person, wherein each reading includes:
  a blood glucose value; and
  a timestamp indicating when the respective reading was taken;
comparing each blood glucose reading of the plurality to a predefined hypoglycemic event threshold, and identifying a hypoglycemic event when a respective blood glucose reading is below the predefined hypoglycemic event threshold;
for at least a subset of the identified hypoglycemic events, prompting the person to provide information associated with each hypoglycemic event using a graphical user interface on the display device, wherein the prompting includes displaying a plurality of hypoglycemic event icons, according to a stored sort order, corresponding to the information requested, and wherein the information requested includes one or more of:
  symptoms associated with the respective hypoglycemic event;
  perceived causes of the respective hypoglycemic event; and
  treatment for the respective hypoglycemic event;
in response to the prompting, obtaining feedback using the graphical user interface on the display device;
updating the stored sort order for the plurality of hypoglycemic event icons based on the obtained feedback; and
providing a report on the display device that includes at least a subset of the obtained feedback.

21. The non-transitory computer readable storage medium of claim 20, wherein the provided report includes a hypo awareness grid, wherein one axis of the grid shows blood glucose level, wherein a second axis of the grid shows reported symptoms, and wherein each entry in the grid indicates how many hypoglycemic events had a specific (glucose level, symptom) pair.

22. The non-transitory computer readable storage medium of claim 20, wherein the provided report includes a graphical presentation of information regarding blood glucose levels before and after one or more hypoglycemic events.

23. The non-transitory computer readable storage medium of claim 20, wherein the provided report includes one or more recommended changes to activities of the person.

24. The non-transitory computer readable storage medium of claim 20, wherein updating the stored sort order for the plurality of hypoglycemic event icons includes sorting the plurality of hypoglycemic event icons according to how commonly each hypoglycemic event icon is selected by the person.

25. The non-transitory computer readable storage medium of claim 20, further comprising:
  transmitting the received blood glucose readings and obtained feedback to a second computing device to identify one or more patterns of hypoglycemic events.

* * * * *